(12) United States Patent
Baumbach et al.

(10) Patent No.: US 12,201,823 B2
(45) Date of Patent: Jan. 21, 2025

(54) LINE DEVICE FOR CONDUCTING A BLOOD FLOW FOR A HEART SUPPORT SYSTEM, HEART SUPPORT SYSTEM, AND METHOD FOR PRODUCING A LINE DEVICE

(71) Applicant: KARDION GMBH, Stuttgart (DE)

(72) Inventors: Hardy Baumbach, Stuttgart (DE); Inga Schellenberg, Stuttgart (DE); David Minzenmay, Stuttgart (DE)

(73) Assignee: Kardion GMBH, Stuttgart (DE)

( * ) Notice: Subject to any disclaimer, the term of this patent is extended or adjusted under 35 U.S.C. 154(b) by 856 days.

(21) Appl. No.: 17/057,411

(22) PCT Filed: May 30, 2019

(86) PCT No.: PCT/EP2019/064138
§ 371 (c)(1),
(2) Date: Jun. 1, 2021

(87) PCT Pub. No.: WO2019/229211
PCT Pub. Date: Dec. 5, 2019

(65) Prior Publication Data
US 2021/0290937 A1   Sep. 23, 2021

(30) Foreign Application Priority Data
May 30, 2018   (DE) .......................... 102018208550.1

(51) Int. Cl.
*A61M 60/859*   (2021.01)
*A61M 60/178*   (2021.01)
(Continued)

(52) U.S. Cl.
CPC ........ *A61M 60/859* (2021.01); *A61M 60/178* (2021.01); *A61M 60/216* (2021.01);
(Continued)

(58) Field of Classification Search
CPC .. A61M 60/859; A61M 60/178; A61M 60/00; A61M 60/80; A61M 60/855; A61M 60/857
See application file for complete search history.

(56) References Cited

U.S. PATENT DOCUMENTS 2,254,698 A   9/1941   Hansen, Jr.
2,310,923 A   2/1943   Bean
(Continued)

FOREIGN PATENT DOCUMENTS

AU   7993698   2/1999
AU   2002308409   12/2005
(Continued)

OTHER PUBLICATIONS

International Preliminary Report on Patentability and Written Opinion received in PCT Application No. PCT/EP2019/064138, dated Dec. 10, 2020 in 13 pages.
(Continued)

*Primary Examiner* — Paula J Stice
(74) *Attorney, Agent, or Firm* — Knobbe, Martens, Olson & Bear, LLP

(57) ABSTRACT

The invention relates to a line device (105) for conducting a blood flow for a heart support system. The heart support system has a head unit and an outlet unit. The line device (105) has a main part (205). The main part (205) has, at a first end, a first attachment section (210) for attaching the line device (105) to the head unit and, at a second end, a second attachment section (215) for attaching the line device (105) to the outlet unit. Furthermore, the main part (205) has a mesh section (220) between the attachment sections (210, 215), wherein the mesh section (220) has a mesh structure (230) formed from at least one mesh wire (225). In addition, the main part (205) has an inlet section (235), arranged in the
(Continued)

first attachment section (210), for introducing the blood flow into the main part (205).

22 Claims, 8 Drawing Sheets

(51) Int. Cl.
 *A61M 60/216* (2021.01)
 *B21C 37/04* (2006.01)
(52) U.S. Cl.
 CPC ... *B21C 37/047* (2013.01); *A61M 2205/0266* (2013.01); *A61M 2207/00* (2013.01)

(56) References Cited

U.S. PATENT DOCUMENTS

| | | |
|---|---|---|
| 3,085,407 A | 4/1963 | Tomlinson |
| 3,505,987 A | 4/1970 | Heilman |
| 3,568,659 A | 3/1971 | Karnegis |
| 3,614,181 A | 10/1971 | Meeks |
| 3,747,998 A | 7/1973 | Klein et al. |
| 3,807,813 A | 4/1974 | Milligan |
| 3,995,617 A | 12/1976 | Watkins et al. |
| 4,115,040 A | 9/1978 | Knorr |
| 4,245,622 A | 1/1981 | Hutchins, IV |
| 4,471,252 A | 9/1984 | West |
| 4,522,194 A | 6/1985 | Normann |
| 4,625,712 A | 12/1986 | Wampler |
| 4,643,641 A | 2/1987 | Clausen et al. |
| 4,753,221 A | 6/1988 | Kensey et al. |
| 4,779,614 A | 10/1988 | Moise |
| 4,785,795 A | 11/1988 | Singh et al. |
| 4,817,586 A | 4/1989 | Wampler |
| 4,846,152 A | 7/1989 | Wampler et al. |
| 4,888,011 A | 12/1989 | Kung et al. |
| 4,889,131 A | 12/1989 | Salem et al. |
| 4,895,557 A | 1/1990 | Moise et al. |
| 4,896,754 A | 1/1990 | Carlson et al. |
| 4,902,272 A | 2/1990 | Milder et al. |
| 4,908,012 A | 3/1990 | Moise et al. |
| 4,927,407 A | 5/1990 | Dorman |
| 4,943,275 A | 7/1990 | Stricker |
| 4,944,722 A | 7/1990 | Carriker et al. |
| 4,968,300 A | 11/1990 | Moutafis et al. |
| 4,971,768 A | 11/1990 | Ealba |
| 4,985,014 A | 1/1991 | Orejola |
| 5,044,897 A | 9/1991 | Dorman |
| 5,061,256 A | 10/1991 | Wampler |
| 5,089,016 A | 2/1992 | Millner et al. |
| 5,090,957 A | 2/1992 | Moutafis et al. |
| 5,112,292 A | 5/1992 | Hwang et al. |
| 5,112,349 A | 5/1992 | Summers et al. |
| 5,116,305 A | 5/1992 | Milder et al. |
| 5,195,877 A | 3/1993 | Kletschka |
| 5,297,940 A | 3/1994 | Buse |
| 5,313,765 A | 5/1994 | Martin |
| 5,344,443 A | 9/1994 | Palma et al. |
| 5,354,271 A | 10/1994 | Voda |
| 5,376,114 A | 12/1994 | Jarvik |
| 5,399,145 A | 3/1995 | Ito et al. |
| 5,405,383 A | 4/1995 | Barr |
| 5,443,503 A | 8/1995 | Yamane |
| 5,456,715 A | 10/1995 | Liotta |
| 5,527,159 A | 6/1996 | Bozeman, Jr. et al. |
| 5,599,173 A | 2/1997 | Chen et al. |
| 5,613,935 A | 3/1997 | Jarvik |
| 5,695,471 A | 12/1997 | Wampler |
| 5,702,430 A | 12/1997 | Larson, Jr. et al. |
| 5,720,771 A | 2/1998 | Snell |
| 5,746,709 A | 5/1998 | Rom et al. |
| 5,749,855 A | 5/1998 | Reitan |
| 5,752,976 A | 5/1998 | Duffin et al. |
| 5,766,207 A | 6/1998 | Potter et al. |
| 5,831,365 A | 11/1998 | Keim et al. |
| 5,888,241 A | 3/1999 | Jarvik |
| 5,888,242 A | 3/1999 | Antaki et al. |
| 5,904,646 A | 5/1999 | Jarvik |
| 5,911,685 A | 6/1999 | Siess et al. |
| 5,921,913 A | 7/1999 | Siess |
| 5,964,694 A | 10/1999 | Siess et al. |
| 6,001,056 A | 12/1999 | Jassawalla et al. |
| 6,007,478 A | 12/1999 | Siess et al. |
| 6,018,208 A | 1/2000 | Maher et al. |
| 6,050,975 A | 4/2000 | Poirier |
| 6,071,093 A | 6/2000 | Hart |
| 6,116,862 A | 9/2000 | Rau et al. |
| 6,123,659 A | 9/2000 | le Blanc et al. |
| 6,135,710 A | 10/2000 | Araki et al. |
| 6,149,405 A | 11/2000 | Abe et al. |
| 6,155,969 A | 12/2000 | Schima et al. |
| 6,158,984 A | 12/2000 | Cao et al. |
| 6,161,838 A | 12/2000 | Balsells |
| 6,176,848 B1 | 1/2001 | Rau et al. |
| 6,186,665 B1 | 2/2001 | Maher et al. |
| 6,210,318 B1 | 4/2001 | Lederman |
| 6,217,541 B1 | 4/2001 | Yu |
| 6,220,832 B1 | 4/2001 | Schob |
| 6,227,820 B1 | 5/2001 | Jarvik |
| 6,245,007 B1 | 6/2001 | Bedingham et al. |
| 6,254,359 B1 | 7/2001 | Aber |
| 6,264,205 B1 | 7/2001 | Balsells |
| 6,264,601 B1 | 7/2001 | Jassawalla et al. |
| 6,264,645 B1 | 7/2001 | Jonkman |
| 6,293,752 B1 | 9/2001 | Clague et al. |
| 6,351,048 B1 | 2/2002 | Schob et al. |
| 6,361,292 B1 | 3/2002 | Chang et al. |
| 6,432,136 B1 | 8/2002 | Weiss et al. |
| 6,445,956 B1 | 9/2002 | Laird et al. |
| 6,447,266 B2 | 9/2002 | Antaki et al. |
| 6,527,698 B1 | 3/2003 | Kung et al. |
| 6,530,876 B1 | 3/2003 | Spence |
| 6,533,716 B1 | 3/2003 | Schmitz-Rode et al. |
| 6,540,658 B1 | 4/2003 | Fasciano et al. |
| 6,544,216 B1 | 4/2003 | Sammler et al. |
| 6,579,257 B1 | 6/2003 | Elgas et al. |
| 6,592,620 B1 | 7/2003 | Lancisi et al. |
| 6,595,743 B1 | 7/2003 | Kazatchkov et al. |
| 6,607,368 B1 | 8/2003 | Ross et al. |
| 6,623,475 B1 | 9/2003 | Siess |
| 6,719,791 B1 | 4/2004 | Nüsser et al. |
| 6,794,789 B2 | 9/2004 | Siess et al. |
| 6,841,910 B2 | 1/2005 | Gery |
| 6,879,126 B2 | 4/2005 | Paden et al. |
| 6,912,423 B2 | 6/2005 | Ley et al. |
| 6,942,611 B2 | 9/2005 | Siess |
| 6,949,066 B2 | 9/2005 | Bearnson et al. |
| 6,969,345 B2 | 11/2005 | Jassawalla et al. |
| 7,014,620 B2 | 3/2006 | Kim |
| 7,022,100 B1 | 4/2006 | Aboul-Hosn et al. |
| 7,027,875 B2 | 4/2006 | Siess et al. |
| 7,011,620 B2 | 5/2006 | Siess |
| 7,070,398 B2 | 7/2006 | Olsen et al. |
| 7,070,555 B2 | 7/2006 | Siess |
| 7,083,588 B1 | 8/2006 | Shmulewitz et al. |
| 7,144,364 B2 | 12/2006 | Barbut et al. |
| 7,160,243 B2 | 1/2007 | Medvedev |
| 7,238,151 B2 | 7/2007 | Frazier |
| 7,241,257 B1 | 7/2007 | Ainsworth et al. |
| 7,264,606 B2 | 9/2007 | Jarvik et al. |
| 7,393,181 B2 | 7/2008 | McBride et al. |
| 7,462,019 B1 | 12/2008 | Allarie et al. |
| 7,479,102 B2 | 1/2009 | Jarvik |
| 7,502,648 B2 | 3/2009 | Okubo et al. |
| 7,736,296 B2 | 6/2010 | Siess et al. |
| 7,762,941 B2 | 7/2010 | Jarvik |
| 7,798,952 B2 | 9/2010 | Tansley et al. |
| 7,841,976 B2 | 11/2010 | McBride et al. |
| 7,850,593 B2 | 12/2010 | Vincent et al. |
| 7,878,967 B1 | 2/2011 | Khanal |
| 7,934,909 B2 | 2/2011 | Jenson |
| 7,914,436 B1 | 3/2011 | Kung |
| 7,959,551 B2 | 6/2011 | Jarvik |
| 7,963,905 B2 | 6/2011 | Salmonsen et al. |

(56) References Cited

U.S. PATENT DOCUMENTS

| | | |
|---|---|---|
| 7,998,190 B2 | 8/2011 | Gharib et al. |
| 8,012,079 B2 | 9/2011 | Delgado, III |
| 8,075,472 B2 | 12/2011 | Zilbershlag et al. |
| 8,088,059 B2 | 1/2012 | Jarvik |
| 8,114,008 B2 | 2/2012 | Hidaka et al. |
| 8,123,669 B2 | 2/2012 | Siess et al. |
| RE43,299 E | 4/2012 | Siess |
| 8,152,845 B2 | 4/2012 | Bourque |
| 8,177,703 B2 | 5/2012 | Smith et al. |
| 8,216,122 B2 | 7/2012 | Kung |
| 8,371,997 B2 | 2/2013 | Shifflette |
| 8,376,926 B2 | 2/2013 | Benkowsi et al. |
| 8,382,695 B1 | 2/2013 | Patel |
| 8,388,565 B2 | 3/2013 | Shifflette |
| 8,419,609 B2 | 4/2013 | Shambaugh, Jr. et al. |
| 8,449,443 B2 | 5/2013 | Rodefeld et al. |
| 8,480,555 B2 | 7/2013 | Kung |
| 8,485,961 B2 | 7/2013 | Campbell et al. |
| 8,512,012 B2 | 8/2013 | Akdis et al. |
| 8,535,211 B2 | 9/2013 | Campbell et al. |
| 8,545,380 B2 | 10/2013 | Farnan et al. |
| 8,562,508 B2 | 10/2013 | Dague et al. |
| 8,585,572 B2 | 11/2013 | Mehmanesh |
| 8,591,393 B2 | 11/2013 | Walters et al. |
| 8,591,538 B2 | 11/2013 | Gellman |
| 8,591,539 B2 | 11/2013 | Gellman |
| 8,597,170 B2 | 12/2013 | Walters et al. |
| 8,617,239 B2 | 12/2013 | Reitan |
| 8,622,949 B2 | 1/2014 | Zafirelis et al. |
| 8,641,594 B2 | 2/2014 | LaRose et al. |
| 8,657,875 B2 | 2/2014 | Kung et al. |
| 8,684,362 B2 | 4/2014 | Balsells et al. |
| 8,684,904 B2 | 4/2014 | Campbell et al. |
| 8,690,749 B1 | 4/2014 | Nunez |
| 8,721,517 B2 | 5/2014 | Zeng et al. |
| 8,727,959 B2 | 5/2014 | Reitan et al. |
| 8,731,664 B2 | 5/2014 | Foster et al. |
| 8,734,331 B2 | 5/2014 | Evans et al. |
| 8,814,933 B2 | 8/2014 | Siess |
| 8,849,398 B2 | 9/2014 | Evans |
| 8,864,642 B2 | 10/2014 | Scheckel |
| 8,864,643 B2 | 10/2014 | Reichenbach et al. |
| 8,864,644 B2 | 10/2014 | Yomtov |
| 8,882,477 B2 | 11/2014 | Fritz, IV et al. |
| 8,888,728 B2 | 11/2014 | Aboul-Hosn et al. |
| 8,894,387 B2 | 11/2014 | White |
| 8,897,873 B2 | 11/2014 | Schima et al. |
| 8,900,060 B2 | 12/2014 | Liebing |
| 8,900,115 B2 | 12/2014 | Bolling et al. |
| 8,932,246 B2 | 1/2015 | Ferrari |
| 8,992,406 B2 | 3/2015 | Corbett |
| 8,992,407 B2 | 3/2015 | Smith et al. |
| 9,028,216 B2 | 5/2015 | Schumacher et al. |
| 9,028,392 B2 | 5/2015 | Shifflette |
| 9,033,863 B2 | 5/2015 | Jarvik |
| 9,091,271 B2 | 7/2015 | Bourque |
| 9,138,518 B2 | 9/2015 | Campbell et al. |
| 9,144,638 B2 | 9/2015 | Zimmermann et al. |
| 9,162,017 B2 | 10/2015 | Evans et al. |
| 9,192,705 B2 | 11/2015 | Yanai et al. |
| 9,199,020 B2 | 12/2015 | Siess |
| 9,265,870 B2 | 2/2016 | Reichenbach et al. |
| 9,297,735 B2 | 3/2016 | Graichen et al. |
| 9,314,556 B2 | 4/2016 | Tuseth |
| 9,327,067 B2 | 5/2016 | Zeng et al. |
| 9,327,068 B2 | 5/2016 | Aboul-Hosn et al. |
| 9,345,824 B2 | 5/2016 | Mohl et al. |
| 9,370,613 B2 | 6/2016 | Hsu et al. |
| 9,371,826 B2 | 6/2016 | Yanai et al. |
| 9,381,286 B2 | 7/2016 | Spence et al. |
| 9,421,311 B2 | 8/2016 | Tanner et al. |
| 9,433,713 B2 | 9/2016 | Corbett et al. |
| 9,440,013 B2 | 9/2016 | Dowling et al. |
| 9,486,566 B2 | 11/2016 | Siess |
| 9,492,601 B2 | 11/2016 | Casas et al. |
| 9,533,084 B2 | 1/2017 | Siess et al. |
| 9,539,378 B2 | 1/2017 | Tuseth |
| 9,550,017 B2 | 1/2017 | Spanier et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,561,313 B2 | 2/2017 | Taskin |
| 9,561,314 B2 | 2/2017 | Aboul-Hosn et al. |
| 9,579,433 B2 | 2/2017 | LaRose et al. |
| 9,585,991 B2 | 3/2017 | Spence |
| 9,592,397 B2 | 3/2017 | Hansen et al. |
| 9,616,157 B2 | 4/2017 | Akdis |
| 9,623,162 B2 | 4/2017 | Graham et al. |
| 9,623,163 B1 | 4/2017 | Fischi |
| 9,636,442 B2 | 5/2017 | Karmon et al. |
| 9,669,144 B2 | 6/2017 | Spanier et al. |
| 9,675,738 B2 | 6/2017 | Tanner et al. |
| 9,675,739 B2 | 6/2017 | Tanner et al. |
| 9,675,740 B2 | 6/2017 | Zeng et al. |
| 9,682,180 B2 | 6/2017 | Hoarau et al. |
| 9,731,058 B2 | 8/2017 | Siebenhaar et al. |
| 9,759,222 B2 | 9/2017 | Zimmermann et al. |
| 9,770,543 B2 | 9/2017 | Tanner et al. |
| 9,789,238 B2 | 10/2017 | Aboul-Hosn et al. |
| 9,801,990 B2 | 10/2017 | Lynch |
| 9,814,813 B2 | 11/2017 | Corbett |
| 9,821,100 B2 | 11/2017 | Corbett et al. |
| 9,833,550 B2 | 12/2017 | Siess |
| 9,849,223 B2 | 12/2017 | LaRose |
| 9,872,948 B2 | 1/2018 | Siess |
| 9,878,087 B2 | 1/2018 | Richardson et al. |
| 9,907,890 B2 | 3/2018 | Muller |
| 9,919,087 B2 | 3/2018 | Pfeffer et al. |
| 9,950,101 B2 | 4/2018 | Smith et al. |
| 9,968,719 B2 | 5/2018 | Colella |
| 9,999,714 B2 | 6/2018 | Spanier et al. |
| 10,029,037 B2 | 7/2018 | Muller et al. |
| 10,123,875 B2 | 11/2018 | Wildhirt et al. |
| 10,124,102 B2 | 11/2018 | Bulent et al. |
| 10,130,742 B2 | 11/2018 | Tuseth |
| 10,149,932 B2 | 12/2018 | McBride et al. |
| 10,179,197 B2 | 1/2019 | Kaiser et al. |
| 10,201,645 B2 | 2/2019 | Muller |
| 10,207,038 B2 | 2/2019 | Neumann |
| 10,220,129 B2 | 3/2019 | Ayre et al. |
| 10,232,099 B2 | 3/2019 | Peters et al. |
| 10,238,782 B2 | 3/2019 | Barry |
| 10,238,783 B2 | 3/2019 | Aboul-Hosn et al. |
| 10,251,986 B2 | 4/2019 | Larose et al. |
| 10,279,093 B2 | 5/2019 | Reichenbach et al. |
| 10,293,090 B2 | 5/2019 | Bonde et al. |
| 10,300,185 B2 | 5/2019 | Aboul-Hosn et al. |
| 10,300,249 B2 | 5/2019 | Tao et al. |
| 10,322,217 B2 | 6/2019 | Spence |
| 10,342,906 B2 | 7/2019 | D'Ambrosio et al. |
| 10,357,598 B2 | 7/2019 | Aboul-Hosn et al. |
| 10,361,617 B2 | 7/2019 | Mueller et al. |
| 10,371,150 B2 | 8/2019 | Wu et al. |
| 10,376,162 B2 | 8/2019 | Edelman et al. |
| 10,420,869 B2 | 9/2019 | Cornen |
| 10,434,232 B2 | 10/2019 | Wu et al. |
| 10,449,275 B2 | 10/2019 | Corbett |
| 10,449,279 B2 | 10/2019 | Muller |
| 10,478,538 B2 | 11/2019 | Scheckel et al. |
| 10,478,539 B2 | 11/2019 | Pfeffer et al. |
| 10,478,542 B2 | 11/2019 | Jahangir |
| 10,500,323 B2 | 12/2019 | Heuring et al. |
| 10,512,537 B2 | 12/2019 | Corbett et al. |
| 10,525,178 B2 | 1/2020 | Zeng |
| 10,537,670 B2 | 1/2020 | Tuseth et al. |
| 10,537,672 B2 | 1/2020 | Tuseth et al. |
| 10,557,475 B2 | 2/2020 | Roehn |
| 10,561,771 B2 | 2/2020 | Heilman et al. |
| 10,561,772 B2 | 2/2020 | Schumacher |
| 10,576,191 B2 | 3/2020 | LaRose |
| 10,584,589 B2 | 3/2020 | Schumacher et al. |
| 10,589,012 B2 | 3/2020 | Toellner et al. |
| 10,589,013 B2 | 3/2020 | Bourque |
| 10,610,626 B2 | 4/2020 | Spanier et al. |

(56) References Cited

U.S. PATENT DOCUMENTS

| | | |
|---|---|---|
| 10,617,808 B2 | 4/2020 | Hastie et al. |
| 10,632,241 B2 | 4/2020 | Schenck et al. |
| 10,660,998 B2 | 5/2020 | Hodges |
| 10,662,967 B2 | 5/2020 | Scheckel |
| 10,668,195 B2 | 6/2020 | Flores |
| 10,669,855 B2 | 6/2020 | Toellner et al. |
| 10,722,631 B2 | 7/2020 | Salahieh et al. |
| 10,773,002 B2 | 9/2020 | Siess et al. |
| 10,814,053 B2 | 10/2020 | Throckmorton et al. |
| 10,857,273 B2 | 12/2020 | Hodges et al. |
| 10,864,308 B2 | 12/2020 | Muller et al. |
| 11,027,114 B2 | 6/2021 | D'Ambrosio et al. |
| 11,033,729 B2 | 6/2021 | Scheckel et al. |
| 11,045,638 B2 | 6/2021 | Keenan et al. |
| 11,058,863 B2 | 7/2021 | Demou |
| 11,058,865 B2 | 7/2021 | Fitzgerald et al. |
| 11,065,434 B2 | 7/2021 | Egler et al. |
| 11,092,158 B2 | 8/2021 | Siess et al. |
| 11,097,092 B2 | 8/2021 | Siess et al. |
| 11,103,689 B2 | 8/2021 | Siess et al. |
| 11,103,690 B2 | 8/2021 | Epple |
| 11,107,626 B2 | 8/2021 | Siess et al. |
| 11,123,538 B2 | 9/2021 | Epple et al. |
| 11,123,539 B2 | 9/2021 | Pfeffer et al. |
| 11,123,541 B2 | 9/2021 | Corbett et al. |
| 11,129,978 B2 | 9/2021 | Pfeffer et al. |
| 11,141,579 B2 | 10/2021 | Steingräber |
| 11,160,970 B2 | 11/2021 | Muller et al. |
| 11,167,124 B2 | 11/2021 | Pfeffer et al. |
| 11,173,297 B2 | 11/2021 | Muller |
| 11,179,557 B2 | 11/2021 | Georges et al. |
| 11,185,678 B2 | 11/2021 | Smith et al. |
| 11,185,680 B2 | 11/2021 | Tuval et al. |
| 11,191,944 B2 | 12/2021 | Tuval et al. |
| 11,197,989 B2 | 12/2021 | Arslan et al. |
| 11,202,901 B2 | 12/2021 | Barry |
| 11,219,756 B2 | 1/2022 | Tanner et al. |
| 11,229,786 B2 | 1/2022 | Zeng et al. |
| 11,235,138 B2 | 2/2022 | Gross-Hardt et al. |
| 11,235,140 B2 | 2/2022 | Siess et al. |
| 11,241,568 B2 | 2/2022 | Keenan et al. |
| 11,241,569 B2 | 2/2022 | Delgado, III |
| 11,253,693 B2 | 2/2022 | Pfeffer et al. |
| 11,260,212 B2 | 3/2022 | Tuval et al. |
| 11,260,213 B2 | 3/2022 | Zeng et al. |
| 11,260,215 B2 | 3/2022 | Scheckel et al. |
| 11,273,300 B2 | 3/2022 | Schafir |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,285,309 B2 | 3/2022 | Tuval et al. |
| 11,291,824 B2 | 4/2022 | Schwammenthal et al. |
| 11,291,825 B2 | 4/2022 | Tuval et al. |
| 11,291,826 B2 | 4/2022 | Tuval et al. |
| 11,298,519 B2 | 4/2022 | Josephy et al. |
| 11,298,520 B2 | 4/2022 | Schwammenthal et al. |
| 11,298,521 B2 | 4/2022 | Schwammenthal et al. |
| 11,298,523 B2 | 4/2022 | Tuval et al. |
| 11,298,524 B2 | 4/2022 | El Katerji et al. |
| 11,298,525 B2 | 4/2022 | Jahangir |
| 11,305,103 B2 | 4/2022 | Larose et al. |
| 11,305,105 B2 | 4/2022 | Corbett et al. |
| 11,311,711 B2 | 4/2022 | Casas et al. |
| 11,311,712 B2 | 4/2022 | Zeng et al. |
| 11,313,228 B2 | 4/2022 | Schumacher et al. |
| D951,435 S | 5/2022 | Motomura et al. |
| 11,318,295 B2 | 5/2022 | Reyes et al. |
| 11,324,940 B2 | 5/2022 | Earles et al. |
| 11,324,941 B2 | 5/2022 | Xu et al. |
| 11,331,465 B2 | 5/2022 | Epple |
| 11,331,466 B2 | 5/2022 | Keen et al. |
| 11,331,467 B2 | 5/2022 | King et al. |
| 11,331,470 B2 | 5/2022 | Muller et al. |
| 11,338,124 B2 | 5/2022 | Pfeffer et al. |
| 11,338,125 B2 | 5/2022 | Liu et al. |
| 11,344,716 B2 | 5/2022 | Taskin |
| 11,344,717 B2 | 5/2022 | Kallenbach et al. |
| 11,351,356 B2 | 6/2022 | Mohl |
| 11,351,357 B2 | 6/2022 | Mohl |
| 11,351,359 B2 | 6/2022 | Clifton et al. |
| 11,357,967 B2 | 6/2022 | Zeng et al. |
| 11,364,373 B2 | 6/2022 | Corbett et al. |
| 11,368,081 B2 | 6/2022 | Vogt et al. |
| 11,369,785 B2 | 6/2022 | Callaway et al. |
| 11,369,786 B2 | 6/2022 | Menon et al. |
| 11,376,415 B2 | 7/2022 | Mohl |
| 11,389,639 B2 | 7/2022 | Casas |
| 11,389,641 B2 | 7/2022 | Nguyen et al. |
| 11,413,443 B2 | 8/2022 | Hodges et al. |
| 11,413,446 B2 | 8/2022 | Siess et al. |
| 11,415,150 B2 | 8/2022 | Richert et al. |
| 11,421,701 B2 | 8/2022 | Schumacher et al. |
| 11,428,236 B2 | 8/2022 | McBride et al. |
| 11,433,168 B2 | 9/2022 | Wu et al. |
| 11,434,921 B2 | 9/2022 | McBride et al. |
| 11,434,922 B2 | 9/2022 | Roehn |
| 11,446,481 B2 | 9/2022 | Wolman et al. |
| 11,446,482 B2 | 9/2022 | Kirchhoff et al. |
| 11,452,859 B2 | 9/2022 | Earles et al. |
| 11,460,030 B2 | 10/2022 | Shambaugh et al. |
| 11,471,662 B2 | 10/2022 | Akkerman et al. |
| 11,471,663 B2 | 10/2022 | Tuval et al. |
| 11,471,665 B2 | 10/2022 | Clifton et al. |
| 11,478,627 B2 | 10/2022 | Siess et al. |
| 11,478,628 B2 | 10/2022 | Muller et al. |
| 11,478,629 B2 | 10/2022 | Harjes et al. |
| 11,484,698 B2 | 11/2022 | Radman |
| 11,484,699 B2 | 11/2022 | Tuval et al. |
| 11,486,400 B2 | 11/2022 | Schumacher |
| 11,491,320 B2 | 11/2022 | Siess |
| 11,491,322 B2 | 11/2022 | Muller et al. |
| 11,497,896 B2 | 11/2022 | Tanner et al. |
| 11,497,906 B2 | 11/2022 | Grace et al. |
| 11,511,101 B2 | 11/2022 | Hastie et al. |
| 11,511,103 B2 | 11/2022 | Salahieh et al. |
| 11,511,104 B2 | 11/2022 | Dur et al. |
| 11,517,726 B2 | 12/2022 | Siess et al. |
| 11,517,736 B2 | 12/2022 | Earles et al. |
| 11,517,737 B2 | 12/2022 | Struthers et al. |
| 11,517,738 B2 | 12/2022 | Wisniewski |
| 11,517,739 B2 | 12/2022 | Toellner |
| 11,517,740 B2 | 12/2022 | Agarwa et al. |
| 11,524,137 B2 | 12/2022 | Jahangir |
| 11,524,165 B2 | 12/2022 | Tan et al. |
| 11,529,062 B2 | 12/2022 | Moyer et al. |
| 11,534,596 B2 | 12/2022 | Schafir et al. |
| 11,565,103 B2 | 1/2023 | Farago et al. |
| 11,569,015 B2 | 1/2023 | Mourran et al. |
| 11,572,879 B2 | 2/2023 | Mohl |
| 11,577,067 B2 | 2/2023 | Breidall et al. |
| 11,577,068 B2 | 2/2023 | Spence et al. |
| 11,583,659 B2 | 2/2023 | Pfeffer et al. |
| 11,583,670 B2 | 2/2023 | Pfeifer et al. |
| 11,583,671 B2 | 2/2023 | Nguyen et al. |
| 11,583,672 B2 | 2/2023 | Weber et al. |
| 11,590,336 B2 | 2/2023 | Harjes et al. |
| 11,590,337 B2 | 2/2023 | Granegger et al. |
| 11,590,338 B2 | 2/2023 | Barry |
| 11,592,028 B2 | 2/2023 | Schumacher et al. |
| 11,596,727 B2 | 3/2023 | Siess et al. |
| 11,602,627 B2 | 3/2023 | Leonhardt |
| 11,617,876 B2 | 4/2023 | Scheckel et al. |
| 11,628,293 B2 | 4/2023 | Gandhi et al. |
| 11,632,015 B2 | 4/2023 | Sconzert et al. |
| 11,633,586 B2 | 4/2023 | Tanner et al. |
| 11,638,813 B2 | 5/2023 | West |
| 11,639,722 B2 | 5/2023 | Medvedev et al. |
| 11,642,511 B2 | 5/2023 | Delgado, III |
| 11,648,387 B2 | 5/2023 | Schwammenthal et al. |
| 11,648,388 B2 | 5/2023 | Siess et al. |
| 11,648,389 B2 | 5/2023 | Wang et al. |
| 11,648,390 B2 | 5/2023 | Spanier et al. |
| 11,648,391 B2 | 5/2023 | Schwammenthal et al. |
| 11,648,392 B2 | 5/2023 | Tuval et al. |

(56) References Cited

U.S. PATENT DOCUMENTS

| | | |
|---|---|---|
| 11,648,393 B2 | 5/2023 | Taskin et al. |
| 11,654,273 B2 | 5/2023 | Granegger et al. |
| 11,654,275 B2 | 5/2023 | Brandt |
| 11,654,276 B2 | 5/2023 | Fitzgerald et al. |
| 11,660,441 B2 | 5/2023 | Fitzgerald et al. |
| 11,666,747 B2 | 6/2023 | Tuval et al. |
| 11,666,748 B2 | 6/2023 | Kronstedt et al. |
| 11,668,321 B2 | 6/2023 | Richert et al. |
| 11,674,517 B2 | 6/2023 | Mohl |
| 11,679,234 B2 | 6/2023 | King et al. |
| 11,679,249 B2 | 6/2023 | Scheckel et al. |
| 11,684,275 B2 | 6/2023 | Tuval et al. |
| 11,684,769 B2 | 6/2023 | Harjes et al. |
| 11,690,521 B2 | 7/2023 | Tuval et al. |
| 11,690,996 B2 | 7/2023 | Siess et al. |
| 11,697,016 B2 | 7/2023 | Epple |
| 11,701,510 B2 | 7/2023 | Demou |
| 11,702,938 B2 | 7/2023 | Schumacher et al. |
| 11,703,064 B2 | 7/2023 | Bredenbreuker et al. |
| 11,708,833 B2 | 7/2023 | McBride et al. |
| 11,744,987 B2 | 9/2023 | Siess et al. |
| 11,745,005 B2 | 9/2023 | Delgado, III |
| 11,746,906 B1 | 9/2023 | Balta et al. |
| 11,752,322 B2 | 9/2023 | Aboulhosn et al. |
| 11,752,323 B2 | 9/2023 | Edwards et al. |
| 11,754,075 B2 | 9/2023 | Schuelke et al. |
| 11,754,077 B1 | 9/2023 | Mohl |
| 11,759,612 B2 | 9/2023 | Tanner et al. |
| 11,759,622 B2 | 9/2023 | Siess et al. |
| 11,766,555 B2 | 9/2023 | Matthes et al. |
| 11,771,884 B2 | 10/2023 | Siess et al. |
| 11,771,885 B2 | 10/2023 | Liu et al. |
| 11,779,234 B2 | 10/2023 | Harjes et al. |
| 11,779,751 B2 | 10/2023 | Earles et al. |
| 11,781,551 B2 | 10/2023 | Yanai et al. |
| 11,786,386 B2 | 10/2023 | Brady et al. |
| 11,786,700 B2 | 10/2023 | Pfeffer et al. |
| 11,786,720 B2 | 10/2023 | Muller |
| 11,793,994 B2 | 10/2023 | Josephy et al. |
| 11,804,767 B2 | 10/2023 | Vogt et al. |
| 11,806,116 B2 | 11/2023 | Tuval et al. |
| 11,806,117 B2 | 11/2023 | Tuval et al. |
| 11,806,517 B2 | 11/2023 | Petersen |
| 11,806,518 B2 | 11/2023 | Michelena et al. |
| 11,813,443 B2 | 11/2023 | Hanson et al. |
| 11,813,444 B2 | 11/2023 | Siess et al. |
| 11,819,678 B2 | 11/2023 | Siess et al. |
| 11,826,127 B2 | 11/2023 | Casas |
| 11,833,278 B2 | 12/2023 | Siess et al. |
| 11,833,342 B2 | 12/2023 | Tanner et al. |
| 11,839,754 B2 | 12/2023 | Tuval et al. |
| 11,844,592 B2 | 12/2023 | Tuval et al. |
| 11,844,940 B2 | 12/2023 | D'Ambrosio et al. |
| 11,850,412 B2 | 12/2023 | Grauwinkel et al. |
| 11,850,413 B2 | 12/2023 | Zeng et al. |
| 11,850,414 B2 | 12/2023 | Schenck et al. |
| 11,850,415 B2 | 12/2023 | Schwammenthal et al. |
| 11,857,743 B2 | 1/2024 | Fantuzzi et al. |
| 11,857,777 B2 | 1/2024 | Earles et al. |
| 11,865,238 B2 | 1/2024 | Siess et al. |
| 11,872,384 B2 | 1/2024 | Cotter |
| 11,883,005 B2 | 1/2024 | Golden et al. |
| 11,883,207 B2 | 1/2024 | El Katerji et al. |
| 11,883,310 B2 | 1/2024 | Nolan et al. |
| 11,883,641 B2 | 1/2024 | Dur et al. |
| 11,890,212 B2 | 2/2024 | Gilmartin et al. |
| 11,896,482 B2 | 2/2024 | Delaloye et al. |
| 11,898,642 B2 | 2/2024 | Stanton et al. |
| 11,904,104 B2 | 2/2024 | Jahangir |
| 11,911,579 B2 | 2/2024 | Tanner et al. |
| 11,918,470 B2 | 3/2024 | Jarral et al. |
| 11,918,496 B2 | 3/2024 | Folan |
| 11,918,726 B2 | 3/2024 | Siess et al. |
| 11,918,800 B2 | 3/2024 | Muller et al. |
| 11,925,356 B2 | 3/2024 | Anderson et al. |
| 11,925,570 B2 | 3/2024 | Lydecker et al. |
| 11,925,794 B2 | 3/2024 | Malkin et al. |
| 11,925,795 B2 | 3/2024 | Muller et al. |
| 11,925,796 B2 | 3/2024 | Tanner et al. |
| 11,925,797 B2 | 3/2024 | Tanner et al. |
| 11,938,311 B2 | 3/2024 | Corbett et al. |
| 11,944,805 B2 | 4/2024 | Stotz |
| 11,980,385 B2 | 5/2024 | Haselman |
| 11,986,604 B2 | 5/2024 | Siess |
| 12,005,248 B2 | 6/2024 | Vogt et al. |
| 12,011,583 B2 | 6/2024 | Wang |
| 12,017,058 B2 | 6/2024 | Kerkhoffs et al. |
| 12,023,476 B2 | 7/2024 | Tuval et al. |
| 12,023,477 B2 | 7/2024 | Siess |
| 12,059,559 B2 | 8/2024 | Muller et al. |
| 12,064,120 B2 | 8/2024 | Hajjar et al. |
| 12,064,611 B2 | 8/2024 | D'Ambrosio et al. |
| 12,064,614 B2 | 8/2024 | Agah et al. |
| 12,064,615 B2 | 8/2024 | Stotz et al. |
| 12,064,616 B2 | 8/2024 | Spanier et al. |
| 12,076,544 B2 | 9/2024 | Siess et al. |
| 12,076,549 B2 | 9/2024 | Stotz et al. |
| 12,090,314 B2 | 9/2024 | Tuval et al. |
| 12,092,114 B2 | 9/2024 | Siess |
| 12,097,016 B2 | 9/2024 | Goldvasser |
| 12,107,474 B2 | 10/2024 | Vollmer |
| 2001/0009645 A1 | 7/2001 | Noda |
| 2001/0041934 A1 | 11/2001 | Yamazaki et al. |
| 2002/0076322 A1 | 6/2002 | Maeda et al. |
| 2002/0147495 A1 | 10/2002 | Petroff |
| 2002/0153664 A1 | 10/2002 | Schroeder |
| 2003/0060685 A1 | 3/2003 | Houser |
| 2003/0091450 A1 | 5/2003 | Davis et al. |
| 2003/0100816 A1 | 5/2003 | Siess |
| 2003/0111800 A1 | 6/2003 | Kreutzer |
| 2003/0139643 A1 | 7/2003 | Smith et al. |
| 2003/0191357 A1 | 10/2003 | Frazier |
| 2004/0044266 A1* | 3/2004 | Siess ............... A61M 60/865 600/16 |
| 2004/0102674 A1 | 5/2004 | Zadini et al. |
| 2004/0115038 A1 | 6/2004 | Nuesser et al. |
| 2004/0167376 A1 | 8/2004 | Peters et al. |
| 2004/0234391 A1 | 11/2004 | Izraelev |
| 2004/0241019 A1 | 12/2004 | Goldowsky |
| 2004/0260346 A1 | 12/2004 | Overall et al. |
| 2005/0006083 A1 | 1/2005 | Chen et al. |
| 2005/0008509 A1 | 1/2005 | Chang |
| 2005/0019167 A1 | 1/2005 | Nusser et al. |
| 2005/0085683 A1 | 4/2005 | Bolling et al. |
| 2005/0220636 A1 | 10/2005 | Henein et al. |
| 2005/0254976 A1 | 11/2005 | Carrier et al. |
| 2006/0030809 A1 | 2/2006 | Barzilay et al. |
| 2006/0062672 A1 | 3/2006 | McBride et al. |
| 2006/0155158 A1 | 7/2006 | Aboul-Hosn |
| 2006/0224110 A1 | 10/2006 | Scott et al. |
| 2006/0276682 A1 | 12/2006 | Bolling et al. |
| 2007/0004959 A1 | 1/2007 | Carrier et al. |
| 2007/0142696 A1 | 6/2007 | Crosby et al. |
| 2007/0156006 A1 | 7/2007 | Smith et al. |
| 2008/0015517 A1 | 1/2008 | Geistert et al. |
| 2008/0058925 A1 | 3/2008 | Cohen |
| 2008/0086027 A1 | 4/2008 | Siess et al. |
| 2008/0114339 A1 | 5/2008 | McBride et al. |
| 2008/0262289 A1 | 10/2008 | Goldowsky |
| 2008/0292478 A1 | 11/2008 | Baykut et al. |
| 2008/0306328 A1 | 12/2008 | Ercolani |
| 2009/0004037 A1 | 1/2009 | Ito |
| 2009/0112312 A1 | 4/2009 | Larose et al. |
| 2009/0203957 A1 | 8/2009 | LaRose et al. |
| 2009/0204205 A1 | 8/2009 | Larose et al. |
| 2010/0041939 A1 | 2/2010 | Siess |
| 2010/0082099 A1 | 4/2010 | Vodermayer et al. |
| 2010/0191035 A1 | 7/2010 | Kang et al. |
| 2010/0268017 A1 | 10/2010 | Siess |
| 2010/0298625 A1 | 11/2010 | Reichenbach et al. |
| 2011/0184224 A1 | 7/2011 | Garrigue |
| 2011/0230821 A1 | 9/2011 | Babic |
| 2011/0237863 A1 | 9/2011 | Ricci et al. |
| 2011/0238172 A1 | 9/2011 | Akdis |

(56) References Cited

U.S. PATENT DOCUMENTS

| | | |
|---|---|---|
| 2012/0029265 A1 | 2/2012 | LaRose |
| 2012/0035645 A1 | 2/2012 | Gross |
| 2012/0088954 A1 | 4/2012 | Foster |
| 2012/0093628 A1 | 4/2012 | Liebing |
| 2012/0134793 A1 | 5/2012 | Wu et al. |
| 2012/0172655 A1 | 7/2012 | Campbell et al. |
| 2012/0178986 A1 | 7/2012 | Campbell et al. |
| 2012/0247200 A1 | 10/2012 | Ahonen et al. |
| 2012/0283506 A1 | 11/2012 | Meister et al. |
| 2012/0310036 A1 | 12/2012 | Peters et al. |
| 2013/0053623 A1 | 2/2013 | Evans |
| 2013/0085318 A1 | 4/2013 | Toellner |
| 2013/0209292 A1 | 8/2013 | Baykut et al. |
| 2013/0281761 A1 | 10/2013 | Kapur |
| 2013/0289376 A1 | 10/2013 | Lang |
| 2013/0303830 A1 | 11/2013 | Zeng et al. |
| 2013/0303831 A1 | 11/2013 | Evans |
| 2013/0303832 A1 | 11/2013 | Wampler |
| 2013/0330219 A1 | 12/2013 | LaRose et al. |
| 2014/0005467 A1 | 1/2014 | Farnan et al. |
| 2014/0051908 A1 | 2/2014 | Khanal et al. |
| 2014/0079557 A1 | 3/2014 | LaRose et al. |
| 2014/0107399 A1 | 4/2014 | Spence |
| 2014/0167545 A1 | 6/2014 | Bremner et al. |
| 2014/0194717 A1 | 7/2014 | Wildhirt et al. |
| 2014/0200389 A1 | 7/2014 | Yanai et al. |
| 2014/0207232 A1 | 7/2014 | Garrigue |
| 2014/0275721 A1 | 9/2014 | Yanai et al. |
| 2014/0330069 A1 | 11/2014 | Hastings et al. |
| 2014/0341726 A1 | 11/2014 | Wu et al. |
| 2015/0031936 A1 | 1/2015 | LaRose et al. |
| 2015/0051435 A1 | 2/2015 | Siess et al. |
| 2015/0051438 A1 | 2/2015 | Taskin |
| 2015/0099923 A1 | 4/2015 | Magovern et al. |
| 2015/0141842 A1 | 5/2015 | Spanier et al. |
| 2015/0171694 A1 | 6/2015 | Dallas |
| 2015/0190092 A1 | 7/2015 | Mori |
| 2015/0273184 A1 | 10/2015 | Scott et al. |
| 2015/0290372 A1 | 10/2015 | Muller et al. |
| 2015/0290373 A1 | 10/2015 | Rudser et al. |
| 2015/0306291 A1 | 10/2015 | Bonde et al. |
| 2015/0343179 A1 | 12/2015 | Schumacher et al. |
| 2015/0365738 A1 | 12/2015 | Purvis et al. |
| 2016/0008531 A1 | 1/2016 | Wang et al. |
| 2016/0030649 A1 | 2/2016 | Zeng |
| 2016/0038663 A1 | 2/2016 | Taskin et al. |
| 2016/0045654 A1 | 2/2016 | Connor |
| 2016/0067395 A1 | 3/2016 | Jimenez et al. |
| 2016/0144089 A1 | 5/2016 | Woo et al. |
| 2016/0144166 A1 | 5/2016 | Decré et al. |
| 2016/0166747 A1 | 6/2016 | Frazier et al. |
| 2016/0213828 A1 | 7/2016 | Sievers |
| 2016/0223086 A1 | 8/2016 | Balsells et al. |
| 2016/0256620 A1 | 9/2016 | Scheckel et al. |
| 2016/0279311 A1 | 9/2016 | Cecere et al. |
| 2016/0367739 A1 | 12/2016 | Wiesener et al. |
| 2016/0375187 A1 | 12/2016 | Lee et al. |
| 2017/0021069 A1 | 1/2017 | Hodges |
| 2017/0021074 A1 | 1/2017 | Opfermann et al. |
| 2017/0035952 A1 | 2/2017 | Muller |
| 2017/0043074 A1 | 2/2017 | Siess |
| 2017/0049947 A1 | 2/2017 | Corbett et al. |
| 2017/0080136 A1 | 3/2017 | Janeczek et al. |
| 2017/0087286 A1 | 3/2017 | Spanier et al. |
| 2017/0087288 A1 | 3/2017 | Groβ-Hardt et al. |
| 2017/0128644 A1 | 5/2017 | Foster |
| 2017/0136225 A1 | 5/2017 | Siess et al. |
| 2017/0143952 A1 | 5/2017 | Siess et al. |
| 2017/0157309 A1 | 6/2017 | Begg et al. |
| 2017/0209633 A1 | 7/2017 | Cohen |
| 2017/0232169 A1 | 8/2017 | Muller |
| 2017/0274128 A1 | 9/2017 | Tamburino et al. |
| 2017/0333607 A1 | 11/2017 | Zarins |
| 2017/0333608 A1 | 11/2017 | Zeng |
| 2017/0340787 A1 | 11/2017 | Corbett et al. |
| 2017/0340788 A1 | 11/2017 | Korakianitis et al. |
| 2017/0340789 A1 | 11/2017 | Bonde et al. |
| 2017/0343043 A1 | 11/2017 | Walsh et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0050141 A1 | 2/2018 | Corbett et al. |
| 2018/0055979 A1 | 3/2018 | Corbett et al. |
| 2018/0064860 A1 | 3/2018 | Nunez et al. |
| 2018/0093070 A1 | 4/2018 | Cottone |
| 2018/0099076 A1 | 4/2018 | LaRose |
| 2018/0110907 A1 | 4/2018 | Keenan et al. |
| 2018/0133379 A1 | 5/2018 | Farnan et al. |
| 2018/0154058 A1 | 6/2018 | Menon et al. |
| 2018/0169312 A1 | 6/2018 | Barry |
| 2018/0169313 A1 | 6/2018 | Schwammenthal et al. |
| 2018/0207336 A1 | 7/2018 | Solem |
| 2018/0219452 A1 | 8/2018 | Boisclair |
| 2018/0221551 A1 | 8/2018 | Tanner et al. |
| 2018/0221553 A1 | 8/2018 | Taskin |
| 2018/0228950 A1 | 8/2018 | Janeczek et al. |
| 2018/0228953 A1 | 8/2018 | Siess et al. |
| 2018/0243004 A1 | 8/2018 | von Segesser et al. |
| 2018/0243489 A1 | 8/2018 | Haddadi |
| 2018/0250456 A1 | 9/2018 | Nitzan et al. |
| 2018/0256797 A1 | 9/2018 | Schenck et al. |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0311421 A1 | 11/2018 | Tuseth |
| 2018/0311423 A1 | 11/2018 | Zeng et al. |
| 2018/0318483 A1 | 11/2018 | Dague et al. |
| 2018/0318547 A1 | 11/2018 | Yokoyama |
| 2018/0326132 A1 | 11/2018 | Maimon et al. |
| 2018/0335037 A1 | 11/2018 | Shambaugh et al. |
| 2018/0345028 A1 | 12/2018 | Aboud et al. |
| 2018/0361042 A1 | 12/2018 | Fitzgerald et al. |
| 2018/0369469 A1 | 12/2018 | Le Duc De Lillers et al. |
| 2019/0001034 A1 | 1/2019 | Taskin et al. |
| 2019/0004037 A1 | 1/2019 | Zhang et al. |
| 2019/0030228 A1 | 1/2019 | Keenan et al. |
| 2019/0046702 A1 | 2/2019 | Siess et al. |
| 2019/0046703 A1 | 2/2019 | Shambaugh et al. |
| 2019/0054223 A1 | 2/2019 | Frazier et al. |
| 2019/0060539 A1 | 2/2019 | Siess et al. |
| 2019/0060543 A1 | 2/2019 | Khanal et al. |
| 2019/0076167 A1 | 3/2019 | Fantuzzi et al. |
| 2019/0083690 A1 | 3/2019 | Siess et al. |
| 2019/0099532 A1 | 4/2019 | Er |
| 2019/0101130 A1 | 4/2019 | Bredenbreuker et al. |
| 2019/0105437 A1 | 4/2019 | Siess et al. |
| 2019/0117865 A1 | 4/2019 | Walters et al. |
| 2019/0125948 A1 | 5/2019 | Stanfield et al. |
| 2019/0143016 A1 | 5/2019 | Corbett et al. |
| 2019/0143018 A1 | 5/2019 | Salahieh et al. |
| 2019/0154053 A1 | 5/2019 | McBride et al. |
| 2019/0167122 A1 | 6/2019 | Obermiller et al. |
| 2019/0167875 A1 | 6/2019 | Simon et al. |
| 2019/0167878 A1 | 6/2019 | Rowe |
| 2019/0170153 A1 | 6/2019 | Scheckel |
| 2019/0175806 A1 | 6/2019 | Tuval et al. |
| 2019/0184078 A1 | 6/2019 | Zilbershlag et al. |
| 2019/0184080 A1 | 6/2019 | Mohl |
| 2019/0192752 A1 | 6/2019 | Tiller et al. |
| 2019/0201603 A1 | 7/2019 | Siess et al. |
| 2019/0209755 A1 | 7/2019 | Nix et al. |
| 2019/0209758 A1 | 7/2019 | Tuval et al. |
| 2019/0211836 A1 | 7/2019 | Schumacher et al. |
| 2019/0211846 A1 | 7/2019 | Liebing |
| 2019/0211847 A1 | 7/2019 | Walsh et al. |
| 2019/0223877 A1 | 7/2019 | Nitzen et al. |
| 2019/0269840 A1 | 9/2019 | Tuval et al. |
| 2019/0275224 A1 | 9/2019 | Hanson et al. |
| 2019/0282741 A1 | 9/2019 | Franano et al. |
| 2019/0282744 A1 | 9/2019 | D'Ambrosio et al. |
| 2019/0282746 A1 | 9/2019 | Judisch |
| 2019/0290817 A1 | 9/2019 | Guo et al. |
| 2019/0298902 A1 | 10/2019 | Siess et al. |
| 2019/0316591 A1 | 10/2019 | Toellner |

(56) References Cited

U.S. PATENT DOCUMENTS

| | | |
|---|---|---|
| 2019/0321527 A1 | 10/2019 | King et al. |
| 2019/0321529 A1 | 10/2019 | Korakianitis et al. |
| 2019/0321531 A1 | 10/2019 | Cambronne et al. |
| 2019/0336664 A1 | 11/2019 | Liebing |
| 2019/0344000 A1 | 11/2019 | Kushwaha et al. |
| 2019/0344001 A1 | 11/2019 | Salahieh et al. |
| 2019/0351117 A1 | 11/2019 | Cambronne et al. |
| 2019/0351119 A1 | 11/2019 | Cambronne et al. |
| 2019/0351120 A1 | 11/2019 | Kushwaha et al. |
| 2019/0358378 A1 | 11/2019 | Schumacher |
| 2019/0358379 A1 | 11/2019 | Wiessler et al. |
| 2019/0358384 A1 | 11/2019 | Epple |
| 2019/0365975 A1 | 12/2019 | Muller et al. |
| 2019/0383298 A1 | 12/2019 | Toellner |
| 2020/0016309 A1 | 1/2020 | Kallenbach et al. |
| 2020/0023109 A1 | 1/2020 | Epple |
| 2020/0030507 A1 | 1/2020 | Higgins et al. |
| 2020/0030509 A1 | 1/2020 | Siess et al. |
| 2020/0030510 A1 | 1/2020 | Higgins |
| 2020/0030511 A1 | 1/2020 | Higgins |
| 2020/0030512 A1 | 1/2020 | Higgins et al. |
| 2020/0038567 A1 | 2/2020 | Siess et al. |
| 2020/0038568 A1 | 2/2020 | Higgins et al. |
| 2020/0038571 A1 | 2/2020 | Jahangir |
| 2020/0069857 A1 | 3/2020 | Schwammenthal et al. |
| 2020/0088207 A1 | 3/2020 | Schumacher et al. |
| 2020/0114053 A1 | 4/2020 | Salahieh et al. |
| 2020/0129684 A1 | 4/2020 | Pfeffer et al. |
| 2020/0139028 A1 | 5/2020 | Scheckel et al. |
| 2020/0139029 A1 | 5/2020 | Scheckel et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0261633 A1 | 8/2020 | Spanier |
| 2020/0345337 A1 | 11/2020 | Muller et al. |
| 2020/0350812 A1 | 11/2020 | Vogt et al. |
| 2021/0052793 A1 | 2/2021 | Struthers et al. |
| 2021/0268264 A1 | 9/2021 | Stotz |
| 2021/0290929 A1 | 9/2021 | Stotz |
| 2021/0290930 A1 | 9/2021 | Kasel |
| 2021/0290932 A1 | 9/2021 | Stotz |
| 2021/0313869 A1 | 10/2021 | Strasswiemer et al. |
| 2021/0316133 A1 | 10/2021 | Kassel et al. |
| 2021/0322756 A1 | 10/2021 | Vollmer et al. |
| 2021/0330958 A1 | 10/2021 | Stotz et al. |
| 2021/0338999 A1 | 11/2021 | Stotz et al. |
| 2021/0339004 A1 | 11/2021 | Schlebusch et al. |
| 2021/0339005 A1 | 11/2021 | Stotz et al. |
| 2021/0346678 A1 | 11/2021 | Baumbach et al. |
| 2021/0379352 A1 | 12/2021 | Schlebusch et al. |
| 2021/0379355 A1 | 12/2021 | Schuelke et al. |
| 2021/0384812 A1 | 12/2021 | Vollmer et al. |
| 2022/0008714 A1 | 1/2022 | Stotz |
| 2022/0016411 A1 | 1/2022 | Winterwerber |
| 2022/0072296 A1 | 3/2022 | Mori |
| 2022/0072297 A1 | 3/2022 | Tuval et al. |
| 2022/0080178 A1 | 3/2022 | Salahieh et al. |
| 2022/0080180 A1 | 3/2022 | Siess et al. |
| 2022/0080182 A1 | 3/2022 | Earles et al. |
| 2022/0080183 A1 | 3/2022 | Earles et al. |
| 2022/0080184 A1 | 3/2022 | Clifton et al. |
| 2022/0080185 A1 | 3/2022 | Clifton et al. |
| 2022/0105337 A1 | 4/2022 | Salahieh et al. |
| 2022/0105339 A1 | 4/2022 | Nix et al. |
| 2022/0126083 A1 | 4/2022 | Grauwinkel et al. |
| 2022/0161018 A1 | 5/2022 | Mitze et al. |
| 2022/0161019 A1 | 5/2022 | Mitze et al. |
| 2022/0161021 A1 | 5/2022 | Mitze et al. |
| 2022/0241580 A1 | 8/2022 | Stotz et al. |
| 2022/0323742 A1 | 10/2022 | Grauwinkel et al. |
| 2023/0001178 A1 | 1/2023 | Corbett et al. |
| 2023/0277833 A1 | 9/2023 | Sharma et al. |
| 2023/0277836 A1 | 9/2023 | Schellenberg et al. |
| 2023/0293878 A1 | 9/2023 | Christof et al. |
| 2023/0364411 A1 | 11/2023 | Bette |
| 2024/0075277 A1 | 3/2024 | Schellenberg |
| 2024/0102475 A1 | 3/2024 | Schuelke et al. |
| 2024/0198084 A1 | 6/2024 | Stotz |
| 2024/0245902 A1 | 7/2024 | Schlebusch et al. |
| 2024/0269459 A1 | 8/2024 | Schellenberg et al. |
| 2024/0277998 A1 | 8/2024 | Vogt et al. |
| 2024/0285935 A1 | 8/2024 | Popov et al. |
| 2024/0335651 A1 | 10/2024 | Mitze et al. |

FOREIGN PATENT DOCUMENTS

| | | |
|---|---|---|
| AU | 2012261669 | 1/2013 |
| AU | 2013203301 | 5/2013 |
| AU | 2013273663 | 1/2014 |
| BR | PI0904483-3 | 7/2011 |
| CA | 2 026 692 | 4/1992 |
| CA | 2 026 693 | 4/1992 |
| CA | 2 292 432 | 5/1998 |
| CA | 2 664 835 | 2/2008 |
| CA | 2 796 357 | 10/2011 |
| CA | 2 947 984 | 11/2022 |
| CN | 1222862 A | 7/1999 |
| CN | 1254598 A | 5/2000 |
| CN | 1376523 A | 10/2002 |
| CN | 2535055 | 2/2003 |
| CN | 1118304 C | 8/2003 |
| CN | 2616217 | 5/2004 |
| CN | 1202871 C | 5/2005 |
| CN | 1833736 A | 9/2006 |
| CN | 200977306 | 11/2007 |
| CN | 101112628 | 1/2008 |
| CN | 101128168 | 2/2008 |
| CN | 201150675 | 11/2008 |
| CN | 101677812 | 3/2010 |
| CN | 201437016 | 4/2010 |
| CN | 201618200 | 11/2010 |
| CN | 201658687 | 12/2010 |
| CN | 201710717 | 1/2011 |
| CN | 201894758 | 7/2011 |
| CN | 102475923 | 5/2012 |
| CN | 102545538 | 7/2012 |
| CN | 202314596 | 7/2012 |
| CN | 102743801 | 10/2012 |
| CN | 103143072 | 6/2013 |
| CN | 103845766 | 6/2014 |
| CN | 103861162 | 6/2014 |
| CN | 203842087 | 9/2014 |
| CN | 104208763 | 12/2014 |
| CN | 104208764 | 12/2014 |
| CN | 203971004 | 12/2014 |
| CN | 104274873 | 1/2015 |
| CN | 204106671 | 1/2015 |
| CN | 204219479 | 3/2015 |
| CN | 103877630 | 2/2016 |
| CN | 205215814 | 5/2016 |
| CN | 103977464 | 8/2016 |
| CN | 104162192 | 9/2016 |
| CN | 104888293 | 3/2017 |
| CN | 106512117 | 3/2017 |
| CN | 104225696 | 6/2017 |
| CN | 107019824 | 8/2017 |
| CN | 206443963 | 8/2017 |
| CN | 107281567 | 10/2017 |
| CN | 104707194 | 11/2017 |
| CN | 107921187 | 4/2018 |
| CN | 105498002 | 6/2018 |
| CN | 106310410 | 7/2018 |
| CN | 106902404 | 8/2019 |
| CN | 209790495 | 12/2019 |
| CN | 110665079 | 1/2020 |
| CN | 210020563 | 2/2020 |
| CN | 111166948 | 5/2020 |
| CN | 111166949 | 5/2020 |
| DE | 1 001 642 | 1/1957 |
| DE | 1 165 144 | 3/1964 |
| DE | 27 07 951 | 9/1977 |
| DE | 26 24 058 | 12/1977 |
| DE | 3 545 214 | 7/1986 |
| DE | 195 46 336 | 5/1997 |

(56) References Cited

FOREIGN PATENT DOCUMENTS

| | | |
|---|---|---|
| DE | 695 01 834 | 10/1998 |
| DE | 198 54 724 | 5/1999 |
| DE | 198 21 307 | 10/1999 |
| DE | 199 10 872 | 10/1999 |
| DE | 199 56 380 | 11/1999 |
| DE | 100 59 714 | 5/2002 |
| DE | 103 45 694 | 4/2005 |
| DE | 697 31 709 | 4/2005 |
| DE | 101 55 011 | 11/2005 |
| DE | 601 19 592 | 9/2006 |
| DE | 11 2004 001 809 | 11/2006 |
| DE | 20 2005 020 288 | 6/2007 |
| DE | 10 2006 019 206 | 10/2007 |
| DE | 10 2006 036 948 | 2/2008 |
| DE | 10 2008 060 357 | 6/2010 |
| DE | 10 2009 039 658 | 3/2011 |
| DE | 20 2009 018 416 | 8/2011 |
| DE | 10 2010 041 995 | 4/2012 |
| DE | 10 2012 022 456 | 5/2014 |
| DE | 10 2013 007 562 | 11/2014 |
| DE | 10 2014 210 299 | 12/2015 |
| DE | 10 2014 212 323 | 12/2015 |
| DE | 11 2014 001 418 | 12/2015 |
| DE | 10 2014 224 151 | 6/2016 |
| DE | 10 2015 216 050 | 2/2017 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2017 209 917 | 12/2018 |
| DE | 10 2017 212 193 | 1/2019 |
| DE | 10 2018 207 564 | 11/2019 |
| DE | 10 2018 207 578 | 11/2019 |
| DE | 10 2018 207 585 | 11/2019 |
| DE | 10 2018 207 591 | 11/2019 |
| DE | 10 2018 207 594 | 11/2019 |
| DE | 10 2018 207 611 | 11/2019 |
| DE | 10 2018 207 622 | 11/2019 |
| DE | 10 2018 208 536 | 12/2019 |
| DE | 10 2018 208 540 | 12/2019 |
| DE | 10 2018 208 541 | 12/2019 |
| DE | 10 2018 208 550 | 12/2019 |
| DE | 10 2018 208 945 | 12/2019 |
| DE | 10 2018 210 076 | 12/2019 |
| DE | 10 2018 207 624 | 1/2020 |
| DE | 10 2018 211 327 | 1/2020 |
| DE | 10 2018 211 328 | 1/2020 |
| DE | 10 2018 212 153 | 1/2020 |
| DE | 10 2018 213 350 | 2/2020 |
| DE | 10 2018 220 658 | 6/2020 |
| DE | 10 2020 102 473 | 8/2021 |
| DE | 11 2020 003 063 | 3/2022 |
| DE | 11 2020 004 148 | 6/2022 |
| EP | 0 050 814 | 5/1982 |
| EP | 0 629 412 | 12/1994 |
| EP | 0 764 448 | 3/1997 |
| EP | 0 855 515 | 7/1998 |
| EP | 0 890 179 | 1/1999 |
| EP | 0 916 359 | 5/1999 |
| EP | 1 013 294 | 6/2000 |
| EP | 1 186 873 | 3/2002 |
| EP | 1 475 880 | 11/2004 |
| EP | 1 169 072 | 5/2005 |
| EP | 1 176 999 | 7/2005 |
| EP | 1 801 420 | 6/2007 |
| EP | 2 009 233 | 12/2008 |
| EP | 2 098 746 | 9/2009 |
| EP | 2 403 109 | 1/2012 |
| EP | 2 187 807 | 6/2012 |
| EP | 3 326 567 | 10/2014 |
| EP | 1 898 971 | 3/2015 |
| EP | 2 519 273 | 8/2015 |
| EP | 2 217 302 | 9/2015 |
| EP | 2 438 936 | 10/2015 |
| EP | 2 438 937 | 10/2015 |
| EP | 2 960 515 | 12/2015 |
| EP | 2 968 718 | 1/2016 |
| EP | 1 996 252 | 5/2016 |
| EP | 2 475 415 | 6/2016 |
| EP | 2 906 265 | 7/2016 |
| EP | 3 069 739 | 9/2016 |
| EP | 1 931 403 | 1/2017 |
| EP | 3 127 562 | 2/2017 |
| EP | 2 585 129 | 3/2017 |
| EP | 3 187 210 | 7/2017 |
| EP | 3 222 301 | 9/2017 |
| EP | 3 222 302 | 9/2017 |
| EP | 3 020 426 | 12/2017 |
| EP | 3 038 669 | 1/2018 |
| EP | 3 062 730 | 1/2018 |
| EP | 3 180 050 | 2/2018 |
| EP | 3 287 154 | 2/2018 |
| EP | 1 789 129 | 6/2018 |
| EP | 2 366 412 | 8/2018 |
| EP | 3 205 359 | 8/2018 |
| EP | 3 205 360 | 8/2018 |
| EP | 3 131 599 | 2/2019 |
| EP | 3 456 367 | 3/2019 |
| EP | 3 119 451 | 6/2019 |
| EP | 3 536 360 | 9/2019 |
| EP | 3 542 835 | 9/2019 |
| EP | 3 542 836 | 9/2019 |
| EP | 3 062 877 | 12/2019 |
| EP | 3 668 560 | 6/2020 |
| EP | 3 711 785 | 9/2020 |
| EP | 3 711 786 | 9/2020 |
| EP | 3 711 787 | 9/2020 |
| EP | 3 720 520 | 10/2020 |
| EP | 3 069 740 | 12/2020 |
| EP | 3 142 722 | 12/2020 |
| EP | 3 579 894 | 12/2020 |
| EP | 3 188 769 | 1/2021 |
| EP | 3 490 122 | 1/2021 |
| EP | 2 869 866 | 2/2021 |
| EP | 3 398 626 | 2/2021 |
| EP | 3 487 549 | 2/2021 |
| EP | 3 113 806 | 3/2021 |
| EP | 3 615 103 | 3/2021 |
| EP | 3 794 720 | 3/2021 |
| EP | 4 271 461 | 3/2021 |
| EP | 2 344 218 | 4/2021 |
| EP | 3 436 104 | 4/2021 |
| EP | 3 749 383 | 4/2021 |
| EP | 3 821 938 | 5/2021 |
| EP | 3 131 615 | 6/2021 |
| EP | 3 338 825 | 6/2021 |
| EP | 3 432 944 | 6/2021 |
| EP | 3 684 439 | 7/2021 |
| EP | 2 582 414 | 8/2021 |
| EP | 3 407 930 | 8/2021 |
| EP | 3 782 665 | 8/2021 |
| EP | 3 782 666 | 8/2021 |
| EP | 3 782 668 | 8/2021 |
| EP | 3 858 397 | 8/2021 |
| EP | 3 216 467 | 9/2021 |
| EP | 3 463 505 | 9/2021 |
| EP | 3 884 968 | 9/2021 |
| EP | 3 884 969 | 9/2021 |
| EP | 3 027 241 | 10/2021 |
| EP | 3 579 904 | 11/2021 |
| EP | 2 628 493 | 12/2021 |
| EP | 3 556 409 | 1/2022 |
| EP | 3 624 868 | 1/2022 |
| EP | 3 955 985 | 2/2022 |
| EP | 3 624 867 | 3/2022 |
| EP | 3 689 389 | 3/2022 |
| EP | 3 697 464 | 3/2022 |
| EP | 3 737 436 | 3/2022 |
| EP | 3 972 661 | 3/2022 |
| EP | 2 967 630 | 4/2022 |
| EP | 3 142 721 | 4/2022 |
| EP | 3 520 834 | 4/2022 |
| EP | 3 586 887 | 4/2022 |

(56) References Cited

FOREIGN PATENT DOCUMENTS

| | | |
|---|---|---|
| EP | 3 638 336 | 4/2022 |
| EP | 3 689 388 | 4/2022 |
| EP | 3 765 110 | 4/2022 |
| EP | 3 782 667 | 4/2022 |
| EP | 3 829 673 | 4/2022 |
| EP | 3 976 129 | 4/2022 |
| EP | 3 984 589 | 4/2022 |
| EP | 3 986 528 | 4/2022 |
| EP | 3 649 926 | 5/2022 |
| EP | 3 653 113 | 5/2022 |
| EP | 3 654 006 | 5/2022 |
| EP | 3 735 280 | 5/2022 |
| EP | 3 897 814 | 5/2022 |
| EP | 3 219 339 | 6/2022 |
| EP | 3 737 310 | 7/2022 |
| EP | 3 899 994 | 8/2022 |
| EP | 3 487 550 | 9/2022 |
| EP | 3 606 575 | 9/2022 |
| EP | 3 834 876 | 9/2022 |
| EP | 3 000 492 | 10/2022 |
| EP | 3 600 477 | 10/2022 |
| EP | 3 897 768 | 10/2022 |
| EP | 3 914 310 | 10/2022 |
| EP | 3 914 311 | 10/2022 |
| EP | 3 000 493 | 11/2022 |
| EP | 3 858 422 | 11/2022 |
| EP | 3 866 876 | 11/2022 |
| EP | 3 941 546 | 11/2022 |
| EP | 2 892 583 | 1/2023 |
| EP | 3 393 542 | 1/2023 |
| EP | 3 597 231 | 1/2023 |
| EP | 3 656 292 | 1/2023 |
| EP | 3 768 345 | 1/2023 |
| EP | 2 868 332 | 2/2023 |
| EP | 3 003 420 | 2/2023 |
| EP | 3 539 585 | 2/2023 |
| EP | 3 956 010 | 2/2023 |
| EP | 3 046 594 | 3/2023 |
| EP | 3 127 563 | 3/2023 |
| EP | 3 256 186 | 3/2023 |
| EP | 3 288 609 | 3/2023 |
| EP | 3 538 173 | 3/2023 |
| EP | 3 606 576 | 3/2023 |
| EP | 3 927 390 | 3/2023 |
| EP | 3 384 940 | 4/2023 |
| EP | 3 441 616 | 4/2023 |
| EP | 3 938 005 | 4/2023 |
| EP | 3 946 511 | 4/2023 |
| EP | 3 544 649 | 6/2023 |
| EP | 3 634 528 | 6/2023 |
| EP | 3 809 959 | 7/2023 |
| EP | 3 912 673 | 7/2023 |
| EP | 2 961 984 | 9/2023 |
| EP | 3 352 808 | 9/2023 |
| EP | 3 554 576 | 10/2023 |
| EP | 3 737 435 | 10/2023 |
| EP | 3 795 208 | 10/2023 |
| EP | 4 052 754 | 10/2023 |
| EP | 4 149 606 | 10/2023 |
| EP | 3 157 596 | 11/2023 |
| EP | 3 515 525 | 11/2023 |
| EP | 3 621 669 | 11/2023 |
| EP | 3 744 362 | 11/2023 |
| EP | 3 766 428 | 11/2023 |
| EP | 3 808 390 | 11/2023 |
| EP | 4 061 470 | 11/2023 |
| EP | 3 449 958 | 12/2023 |
| EP | 3 687 596 | 12/2023 |
| EP | 3 710 076 | 12/2023 |
| EP | 3 768 340 | 12/2023 |
| EP | 3 787 707 | 12/2023 |
| EP | 3 926 194 | 12/2023 |
| EP | 3 784 305 | 1/2024 |
| EP | 3 801 675 | 1/2024 |
| EP | 3 925 659 | 1/2024 |
| EP | 4 115 919 | 1/2024 |
| EP | 3 634 526 | 2/2024 |
| EP | 3 768 342 | 2/2024 |
| EP | 3 768 347 | 2/2024 |
| EP | 3 769 799 | 2/2024 |
| EP | 3 790 606 | 2/2024 |
| EP | 3 930 780 | 2/2024 |
| EP | 3 782 695 | 3/2024 |
| EP | 3 854 448 | 3/2024 |
| EP | 4 140 532 | 5/2024 |
| EP | 3 693 038 | 6/2024 |
| EP | 3 768 344 | 7/2024 |
| EP | 3 970 765 | 7/2024 |
| EP | 3 854 444 | 9/2024 |
| FR | 1458525 | 3/1966 |
| FR | 2 768 056 | 3/1999 |
| GB | 0 648 739 | 1/1951 |
| GB | 2 213 541 | 8/1989 |
| GB | 2 345 387 | 7/2000 |
| GB | 2 451 161 | 12/2011 |
| GB | 2 545 062 | 6/2017 |
| GB | 2 545 750 | 6/2017 |
| JP | 59-119788 | 8/1984 |
| JP | S61-500059 | 1/1986 |
| JP | S62-113555 | 7/1987 |
| JP | S64-68236 | 3/1989 |
| JP | H02-055886 | 2/1990 |
| JP | 2-79738 | 3/1990 |
| JP | H04-176471 | 6/1992 |
| JP | H04-108384 | 9/1992 |
| JP | H08-057042 | 3/1996 |
| JP | H10-052489 | 2/1998 |
| JP | 2888609 | 5/1999 |
| JP | 2889384 | 5/1999 |
| JP | H11-239617 | 9/1999 |
| JP | 2001-037728 | 2/2001 |
| JP | 2001-515374 | 9/2001 |
| JP | 2001-515375 | 9/2001 |
| JP | 2003-019197 | 1/2003 |
| JP | 2003-525438 | 8/2003 |
| JP | 2004-019468 | 1/2004 |
| JP | 2004-278375 | 10/2004 |
| JP | 2005-028137 | 2/2005 |
| JP | 2005-507039 | 3/2005 |
| JP | 2008-511414 | 4/2008 |
| JP | 2008-516654 | 5/2008 |
| JP | 2010-518907 | 6/2010 |
| JP | 2010-258181 | 11/2010 |
| JP | 2010-534080 | 11/2010 |
| JP | 2013-013216 | 1/2013 |
| JP | 2013-519497 | 5/2013 |
| JP | 2014-004303 | 1/2014 |
| JP | 2014-524274 | 9/2014 |
| JP | 2015-514529 | 5/2015 |
| JP | 2015-514531 | 5/2015 |
| JP | 2015-122448 | 7/2015 |
| JP | 2016-002466 | 1/2016 |
| JP | 2016-532500 | 10/2016 |
| JP | 6063151 | 1/2017 |
| JP | 6267625 | 1/2018 |
| JP | 2018-057878 | 4/2018 |
| JP | 6572056 | 9/2019 |
| JP | 2020-072985 | 5/2020 |
| JP | 2018-510708 | 3/2021 |
| KR | 10-2011-0098192 | 9/2011 |
| RO | 131676 | 2/2017 |
| RU | 2 051 695 | 1/1996 |
| TW | 374317 | 11/1999 |
| UA | 97202 C2 | 1/2012 |
| WO | WO 94/009835 | 5/1994 |
| WO | WO 97/037696 | 10/1997 |
| WO | WO 97/039785 | 10/1997 |
| WO | WO 99/049912 | 10/1999 |
| WO | WO 00/033446 | 6/2000 |
| WO | WO 02/022200 | 3/2002 |
| WO | WO 02/041935 | 5/2002 |
| WO | WO 02/070039 | 9/2002 |
| WO | WO 03/075981 | 9/2003 |
| WO | WO 03/103745 | 12/2003 |

(56) References Cited

FOREIGN PATENT DOCUMENTS

| | | |
|---|---|---|
| WO | WO 2005/020848 | 3/2005 |
| WO | WO 2005/028014 | 3/2005 |
| WO | WO 2005/037345 | 4/2005 |
| WO | WO 2007/033933 | 3/2007 |
| WO | WO 2007/105842 | 9/2007 |
| WO | WO 2008/017289 | 2/2008 |
| WO | WO 2008/081783 | 7/2008 |
| WO | WO 2009/010888 | 1/2009 |
| WO | WO 2009/046789 | 4/2009 |
| WO | WO 2009/046790 | 4/2009 |
| WO | WO 2009/073037 | 6/2009 |
| WO | WO 2010/119267 | 10/2010 |
| WO | WO 2011/003043 | 1/2011 |
| WO | WO 2011/081626 | 7/2011 |
| WO | WO 2011/160858 | 12/2011 |
| WO | WO 2012/018917 | 2/2012 |
| WO | WO 2012/047540 | 4/2012 |
| WO | WO 2012/112129 | 8/2012 |
| WO | WO 2013/037380 | 3/2013 |
| WO | WO 2013/120957 | 8/2013 |
| WO | WO 2013/167432 | 11/2013 |
| WO | WO 2013/173239 | 11/2013 |
| WO | WO 2015/039605 | 3/2015 |
| WO | WO 2015/063281 | 5/2015 |
| WO | WO 2015/085076 | 6/2015 |
| WO | WO 2015/109028 | 7/2015 |
| WO | WO 2015/172173 | 11/2015 |
| WO | WO 2015/175718 | 11/2015 |
| WO | WO 2016/028644 | 2/2016 |
| WO | WO 2016/137743 | 9/2016 |
| WO | WO 2016/146661 | 9/2016 |
| WO | WO 2016/146663 | 9/2016 |
| WO | WO 2017/004175 | 1/2017 |
| WO | WO 2017/015764 | 2/2017 |
| WO | WO 2017/021465 | 2/2017 |
| WO | WO 2017/053988 | 3/2017 |
| WO | WO 2017/060257 | 4/2017 |
| WO | WO 2017/112695 | 6/2017 |
| WO | WO 2017/112698 | 6/2017 |
| WO | WO 2017/147291 | 8/2017 |
| WO | WO 2017/159849 | 9/2017 |
| WO | WO 2017/162619 | 9/2017 |
| WO | WO 2017/205909 | 12/2017 |
| WO | WO 2018/007120 | 1/2018 |
| WO | WO 2018/036927 | 3/2018 |
| WO | WO 2018/088939 | 3/2018 |
| WO | WO 2018/081040 | 5/2018 |
| WO | WO 2018/089970 | 5/2018 |
| WO | WO 2018/109038 | 6/2018 |
| WO | WO 2018/139508 | 8/2018 |
| WO | WO 2018/197306 | 11/2018 |
| WO | WO 2019/034670 | 2/2019 |
| WO | WO 2019/035804 | 2/2019 |
| WO | WO 2019/038343 | 2/2019 |
| WO | WO 2019/057636 | 3/2019 |
| WO | WO 2019/067233 | 4/2019 |
| WO | WO 2019/078723 | 4/2019 |
| WO | WO 2019/135767 | 7/2019 |
| WO | WO 2019/137911 | 7/2019 |
| WO | WO 2019/138350 | 7/2019 |
| WO | WO 2019/145253 | 8/2019 |
| WO | WO 2019/158996 | 8/2019 |
| WO | WO 2019/161245 | 8/2019 |
| WO | WO 2019/180104 | 9/2019 |
| WO | WO 2019/180179 | 9/2019 |
| WO | WO 2019/180181 | 9/2019 |
| WO | WO 2018/135477 | 11/2019 |
| WO | WO 2018/135478 | 11/2019 |
| WO | WO 2019/211410 | 11/2019 |
| WO | WO 2019/219868 | 11/2019 |
| WO | WO 2019/219871 | 11/2019 |
| WO | WO 2019/219872 | 11/2019 |
| WO | WO 2019/219874 | 11/2019 |
| WO | WO 2019/219876 | 11/2019 |
| WO | WO 2019/219881 | 11/2019 |
| WO | WO 2019/219882 | 11/2019 |
| WO | WO 2019/219883 | 11/2019 |
| WO | WO 2019/219884 | 11/2019 |
| WO | WO 2019/219885 | 11/2019 |
| WO | WO 2019/229210 | 12/2019 |
| WO | WO 2019/229211 | 12/2019 |
| WO | WO 2019/229214 | 12/2019 |
| WO | WO 2019/229220 | 12/2019 |
| WO | WO 2019/229221 | 12/2019 |
| WO | WO 2019/229222 | 12/2019 |
| WO | WO 2019/229223 | 12/2019 |
| WO | WO 2019/234146 | 12/2019 |
| WO | WO 2019/239259 | 12/2019 |
| WO | WO 2019/241556 | 12/2019 |
| WO | WO 2019/243582 | 12/2019 |
| WO | WO 2019/243588 | 12/2019 |
| WO | WO 2020/003110 | 1/2020 |
| WO | WO 2020/011760 | 1/2020 |
| WO | WO 2020/011795 | 1/2020 |
| WO | WO 2020/011797 | 1/2020 |
| WO | WO 2020/016438 | 1/2020 |
| WO | WO 2020/028312 | 2/2020 |
| WO | WO 2020/028537 | 2/2020 |
| WO | WO 2020/030700 | 2/2020 |
| WO | WO 2020/064911 | 4/2020 |
| WO | WO 2020/073047 | 4/2020 |
| WO | WO 2020/132211 | 6/2020 |
| WO | WO 2020/176236 | 9/2020 |
| WO | WO 2020/187797 | 9/2020 |
| WO | WO 2020/219430 | 10/2020 |
| WO | WO 2020/234785 | 11/2020 |
| WO | WO 2020/242881 | 12/2020 |
| WO | WO 2021/046275 | 3/2021 |
| WO | WO 2021/062265 | 4/2021 |
| WO | WO 2021/067691 | 4/2021 |
| WO | WO 2021/119478 | 6/2021 |
| WO | WO 2021/150777 | 7/2021 |
| WO | WO 2021/152013 | 8/2021 |
| WO | WO 2022/056542 | 3/2022 |
| WO | WO 2022/063650 | 3/2022 |
| WO | WO 2022/072944 | 4/2022 |
| WO | WO 2022/076862 | 4/2022 |
| WO | WO 2022/076948 | 4/2022 |
| WO | WO 2022/109589 | 5/2022 |
| WO | WO 2022/109590 | 5/2022 |
| WO | WO 2022/109591 | 5/2022 |
| WO | WO 2022/173970 | 8/2022 |
| WO | WO 2022/174249 | 8/2022 |
| WO | WO 2023/278599 | 1/2023 |
| WO | WO 2023/014742 | 2/2023 |
| WO | WO 2023/049813 | 3/2023 |
| WO | WO 2023/076869 | 5/2023 |
| WO | WO 2023/230157 | 11/2023 |

OTHER PUBLICATIONS

International Search Report and Written Opinion received in PCT Application No. PCT/EP2019/064138, dated Sep. 16, 2019 in 17 pages.
"ABMD—Taking a Closer Look at Impella ECP as the Pivotal Trial Gets Underway", Guggenheim, Press Release, Mar. 29, 2022, pp. 4.
Escudeiro et al., "Tribological behavior of uncoated and DLC-coated CoCr and Ti-alloys in contact with UHMWPE and PEEK counterbodies;" Tribology International, vol. 89, 2015, pp. 97-104.
Hinkel et al., "Pump Reliability and Efficiency Increase Maintenance Program—Utilizing High Performance Thermoplastics;" Proceedings of the 16th International Pump Users Symposium, Texas A&M University. Turbomachinery Laboratories; 1999, pp. 115-120.
Neale, Michael J., "The Tribology Handbook;" 1999, Butterworth-Heinemann, Second Edition, pp. 582.
Park et al., "A Novel Electrical Potential Sensing Method for in Vitro Stent Fracture Monitoring and Detection", Jan. 1, 2011, vol. 21, No. 4, pp. 213-222.
Sak et al., "Influence of polyetheretherketone coatings on the Ti—13Nb—13Zr titanium alloy's bio-tribological properties and corrosion resistance;" Materials Science and Engineering: C, vol. 63, 2016, pp. 52-61.

(56) References Cited

OTHER PUBLICATIONS

Vollkron et al., "Advanced Suction Detection for an Axial Flow Pump", Artificial Organs, 2006, vol. 30, No. 9, pp. 665-670.
Vollkron et al., "Development of a Suction Detection System for Axial Blood Pumps", Artificial Organs, 2004, vol. 28, No. 8, pp. 709-716.
Ai, X. (2013). Radial Bearings. In: Wang, Q.J., Chung, YW. (eds) Encyclopedia of Tribology. Springer, Boston, MA https://doi.org/10.1007/978-0-387-92897-5_334, accessed Oct. 18, 2024, pp. 4.
"Edwards Sapien 3 Kit—Transapical and Transaortic", Edwards Lifesciences, Released Nov. 8, 2016, pp. 11. chrome-extension://efaidnbmnnnibpcajpcglclefindmkaj/https://edwardsprod.blob.core.windows.net/media/De/sapien3/doc-0045537b%20-%20certitude.pdf.
GGB by Timken Bearings FAQ; "What is a Slide Bearing?;" https://www.ggbearings.com/en/why-choose-ggb/faq/bearings-faq/what-slide-bearing; accessed Oct. 10, 2024, pp. 1.
Google.com, "Spider Bearing—Search Results;" https://www.google.com/search?q=spider+bearing&rlz=X1C1GCEA_enUS1059US1059&oq=spider+beari&gs_lcrp=EgZjaHJvbWUqCQgAEEUYOxiABDIJCAAQRRg7GIAEMgYIARBFGDkyBwgCEAAY gAQyBwgDEAAYgAQyBwgEEAAYgAQyBwgFEAAYgAQyBwgGEAAYgAQyBggHEEUYPKgCALACAA&sourceid=chrome&ie=UTF-8, accessed Oct. 18, 2024, pp. 4.
Gopinath, Divya, "A System for Impedance Characterization of Coronary Stents", University of Strathclyde Engineering, Thesis, Aug. 2015, pp. 77.
McMaster-Carr Online Catalog, "Bearings search results;" https://www.mcmaster.com/products/bearings/; accessed Oct. 18, 2024, pp. 5.
McMaster-Carr Online Catalog, "Slide Bearings search results;" https://www.mcmaster.com/products/slide-bearings/; accessed Oct. 18, 2024, pp. 21.
RBCbearings.com, "RBC Bearings Incorporated—Products;" https://www.rbcbearings.com/Products; accessed Oct. 18, 2024, pp. 2.
SKF.com; "Products: Bearings;" https://www.skf.com/us/products/bearings; accessed Oct. 18, 2024, pp. 8.
Wikipedia, "Plain Bearing," https://en.wikipedia.org/wiki/Plain_bearing; accessed Oct. 18, 2024, pp. 10.

\* cited by examiner

LINE DEVICE FOR CONDUCTING A BLOOD FLOW FOR A HEART SUPPORT SYSTEM, HEART SUPPORT SYSTEM, AND METHOD FOR PRODUCING A LINE DEVICE

BACKGROUND

Field

The invention relates to a device or a method for conducting a blood flow for a heart support system.

Description of the Related Art

Heart support systems, in particular left ventricular support systems, can be differentiated with regard to their position on the heart and their access to blood circulation. Long-term support systems can be positioned at the apex of the heart (transapically) and bridge the left heart chamber by pumping blood from the apex of the heart through a tube directly into the aorta. Another type of access can be used in particular for short-term support of the heart; for example, the heart support system can be a ventricular support system as a bridging measure for bridging until transplantation (bridge to decision, bridge to transplant). In this case, the natural aortic valve can be used to create a connection between the pump inlet and the pump outlet. In such an arrangement of the heart support system, the aorta can be used as an access route (transaortally) within the scope of minimally invasive surgery, and sternotomy can be avoided.

SUMMARY

The invention is based on the object of specifying an improved line device for a heart support system, in particular with permanent connection reliability and suitable flexibility, as well as a method for its production.

In light of this background, the approach presented here presents a line device for conducting a blood flow for a heart support system, a heart support system, and a method for producing a line device according to the main claims. Advantageous developments and improvements of the device specified in the independent claim are possible by means of the measures listed in the dependent claims.

This approach presents a line device for conducting a blood flow for a heart support system, e.g., a left ventricular heart support system. The line device can be used as a flow channel in which the blood flow from the pump inlet in a left heart chamber can be conducted to the pump outlet within an aorta. The line device can have two attachment sections for attaching further components of the heart support system, and also a mesh section of at least one mesh wire arranged between the attachment sections. An advantageous ratio of flexibility and stiffness of the line device can be adjusted by means of the mesh structure of the mesh section. This is advantageous in order to allow transfemoral surgery (access via the groin) in order to implant the heart support system.

A line device for conducting a blood flow for a heart support system is presented. The heart support system has a head unit and an outlet unit. The line device has a main part, wherein the main part has, at a first end, a first attachment section for attaching the line device to the head unit and, at a second end, a second attachment section for attaching the line device to the outlet unit. The main part furthermore has a mesh section between the attachment sections. The mesh section has a mesh structure formed from at least one mesh wire. In addition, the main part has an inlet section, arranged in the first attachment section, for introducing the blood flow into the main part.

The line device can, for example, be formed from a biocompatible material and understood as a flow channel for the flexible connection of components of a heart support system for conducting a blood flow between the ventricle and the blood vessel. The line device can be used as a suction tube of the heart support system in order to introduce the blood flow and to conduct it further to an outlet section of the heart support system. For example, the heart support system can be understood to be a left ventricular support system (LVAD, left ventricular assist device) or another ventricular support system (VAD, ventricular assist device). The main part of the line device can, for example, be formed as a hollow cylinder and essentially have a pipe geometry. The main part can be formed in one piece or be constructed modularly; the main part can, for example, also be composed of the first attachment section, the mesh section, and the second attachment section. The first attachment section at a first end of the main part can be understood as a distal attachment section and be, for example, arranged in the implanted state of the heart support system as a left ventricular support system in the left heart chamber. The second attachment section at a second end of the main part can be understood as a proximal attachment section and be, for example, arranged in the implanted state of the left ventricular support system in the aorta. A head unit of the heart support system, e.g., a sensor assembly, can be attached to the first attachment section. The mesh section can, for example, be a main part section with a braided mesh structure for adjusting the flexibility and stiffness of the line device, wherein a stiffness of the mesh section is dependent on the mesh structure. Adjusting a predefined stiffness is advantageous in order to allow use of the line device during transfemoral surgery, for example. The flexibility and the stiffness of the mesh section can be adjusted, for example, by means of a number, a stiffness, or a material thickness of the at least one mesh wire, as well as by means of a mesh pattern of the mesh structure. The inlet section can be realized, for example, by a multi-part window in the first attachment section in order to allow the blood flow to be introduced into the main part of the line device.

According to one embodiment, at least one of the attachment sections can have at least one eyelet for threading an end of the at least one mesh wire in order to connect the mesh section to the respective attachment section. For example, the first attachment section can have the at least one eyelet, or the second attachment section can have the at least one eyelet, or the first attachment section and the second attachment section can respectively have at least one eyelet. The eyelet can, for example, be a hook eye or it can be realized as a bore in the respective attachment section. The eyelet can, for example, be realized on the side of the respective attachment section facing the mesh section. At least one of the attachment sections can also have a plurality of eyelets in order to, for example, connect several wire loops of the mesh wire to the respective attachment section. The mesh section can advantageously be easily and securely connected to the attachment section by means of the at least one eyelet.

In addition, according to one embodiment, the first attachment section can have at least one merlon. The merlon can in particular be arranged on the side of the first attachment section facing the mesh section. Additionally or alternatively, the second attachment section can have at least one merlon. In particular, the merlon can be arranged on the side of the second attachment section facing the mesh section. The at least one merlon can, for example, be formed as a projection of the respective attachment section. The merlon can, for example, also be formed to engage in the mesh section or on the mesh section. The at least one merlon can advantageously additionally fix the mesh section.

If at least one of the attachment sections according to one embodiment has at least one merlon, the at least one eyelet can be formed in the merlon. The eyelet can, for example, be designed to allow tangential threading of the mesh wire. The eyelet can, for example, have a longitudinal extension axis, which extends tangentially with respect to a circumference of the attachment section. At least one of the attachment sections can also have a plurality of merlons, wherein in this case at least one of the merlons or several merlons can have the at least one eyelet. The merlons can, for example, be arranged circumferentially and evenly spaced around the circumference of the attachment section.

The mesh structure of the mesh section can be formed as a diamond lattice according to one embodiment. The mesh structure can, for example, be braided from the at least one mesh wire, wherein the diamond lattice is formed from meshes of the mesh wire. The diamond shape can correspond to a standard shape of a vascular stent, which is advantageous with respect to the production of the mesh structure.

Furthermore, according to one embodiment, the mesh section can be formed to accommodate and/or guide a cable element of the heart support system. The cable element can, for example, be a section of a cable for signal and energy transmission. If the head unit of the heart support system has a sensor, for example, the cable element can be part of a sensor cable. The cable element can, for example, be braided into the mesh structure, or the cable element can, for example, be guided circumferentially around the mesh section along the mesh section; in this case, the cable element can be glued on, for example. This embodiment advantageously allows compact design. The mesh section can advantageously also provide mechanical protection from cable breakage.

If the mesh section is formed to accommodate the cable element, the mesh structure according to one embodiment can be formed from the at least one mesh wire and the cable element. The cable element can, for example, additionally be braided into the mesh structure. If the mesh structure is formed from at least two mesh wires, the cable element can also be used instead of one of the two mesh wires. For example, the mesh structure can in this case be formed, and one of the mesh wires can subsequently be removed and replaced by the cable element. This embodiment is also advantageous in terms of a compact design and protection of the cable element from cable breakage.

In addition, at least the mesh section can according to one embodiment be formed from a shape memory material. The shape memory material can be a biocompatible shape memory polymer, or a biocompatible shape memory alloy, such as Nitinol for example. Furthermore, the entire main part can also be manufactured from the shape memory material. The use of Nitinol as a shape memory material is advantageous since the Nitinol material is a proven material in medicine, in particular in the field of cardiovascular medicine, e.g., for heart valve prostheses, stents, and vascular prostheses, and, due to its biocompatibility and the shape memory property, allows even complex structures to be realized in a small installation space.

According to one embodiment, the mesh section extends over at least half of the main part in order to adjust the stiffness of the main part. This is advantageous with regard to implantation of the line device, in particular in the case of transfemoral access, in order to make possible a predefined ratio of flexibility and stiffness of the line device as a result of the forming the mesh section. The flexibility of the line device can be advantageous, for example, when pushing through an aortic bend, and the stiffness can advantageously prevent the line device from kinking when pushing through a blood vessel.

According to one embodiment, the line device can also have a sealing layer. The sealing layer can be arranged on or in the mesh section and be formed to fluid-tightly seal the mesh section. The fluid-tight sealing of the mesh section by means of the sealing layer is advantageous for conducting the blood flow in order to conduct the blood flow to the outlet unit without loss. The sealing section can be realized, for example, by casting or injection-molding the mesh section with a flexible plastic, such as polyurethane or silicone.

In addition, the mesh section can according to one embodiment have a bending point. The mesh section can in particular be bent at an obtuse angle at the bending point. The bending point can, for example, be formed in the center of the mesh section or be arranged closer to the first attachment section than to the second attachment section. The mesh section can, for example, have a first longitudinal axis between one end in the direction of the second attachment section and the bending point and have a second longitudinal axis obliquely to the first between the bending point and a second end in the direction of the first attachment section. At the bending point, an angle between the first and the second longitudinal axis can, for example, be between 20 degrees and 30 degrees, in particular 26 degrees. The bending point can, for example, be formed to give the main part a curved shape corresponding to human anatomy in order to allow the inlet section to be positioned in the center of a heart chamber in order to advantageously prevent the inlet unit from being sucked to a heart chamber wall.

Furthermore, according to one embodiment, an inner diameter of the main part can change from the first attachment section to the second attachment section. For example, a cross section of the inner diameter can taper in the direction of the second attachment section. The change in the inner diameter of the main part can advantageously improve the flow properties of the introduced blood flow.

According to one embodiment, the inlet section can have at least one inlet opening cut in the first attachment section. The inlet opening can, for example, be formed rectangularly or as a rectangle with a circular arc in the direction of the structural section. The inlet section can also have several inlet openings, e.g., three inlet openings. In this case, the inlet openings can be evenly spaced, for example, wherein, between two adjacent inlet openings, a narrow bridge can, for example, connect the first attachment section to the structural section. By forming at least one inlet opening, which can be cut in or into the main part, an additional structural element for introducing the blood flow can advantageously be dispensed with, which is advantageous with regard to a compact design.

A heart support system is also presented. The heart support system can have a head unit, an outlet unit, and an embodiment of the aforementioned line device. The line device can be arranged between the head unit and the outlet unit and connected to the head unit and the outlet unit.

A method for producing a line device for conducting a blood flow for a heart support system is also presented. The heart support system can have a head unit and an outlet unit. The method comprises the following steps:

forming a main part made of a semi-finished product made of a shape memory material, wherein the main part has, at a first end, a first attachment section for attaching the line device to the head unit and, at a second end, a second attachment section for attaching the line device to the outlet unit, wherein the main part has a mesh section between the attachment sections, wherein the mesh section has a mesh structure formed from at least one mesh wire, wherein the main part has an inlet section, arranged in the first attachment section, for introducing the blood flow into the main part; and heat treating the formed main part in order to emboss a predefined shape into the main part.

By carrying out the aforementioned method, an embodiment of the aforementioned line device can advantageously be produced.

BRIEF DESCRIPTION OF THE DRAWINGS

Exemplary embodiments of the approach presented here are shown in the drawings and explained in more detail in the following description. They show.

DETAILED DESCRIPTION

In the following description of favorable exemplary embodiments of the present invention, the same or similar reference signs are used for the elements which are shown in the various figures and have a similar effect, wherein a repeated description of these elements is omitted.

Figure 1:
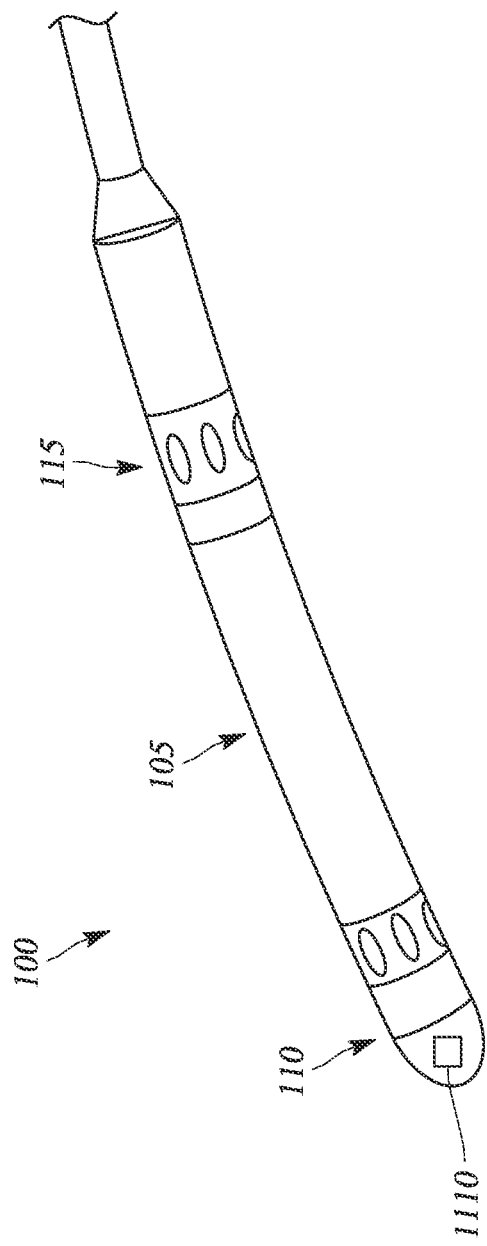
FIG. 1 a schematic illustration of a heart support system with a line device for conducting a blood flow according to an exemplary embodiment.

FIG. 1 shows a schematic illustration of a heart support system 100 with a line device 105 for conducting a blood flow according to an exemplary embodiment. Shown is a side view of the heart support system 100 as a whole system, which is designed here, by way of example, as a left ventricular support system 100. The heart support system 100 comprises a head unit 110, an outlet unit 115, and the line device 105. The line device 105 is arranged between the head unit 110 and the outlet unit 115 and is connected to the head unit 110 and the outlet unit 115. The line device 105 can also be referred to as a suction tube, which connects a pump inlet within a heart chamber to an outlet within the aorta in the implanted state of the heart support system 100.

The heart support system 100 has a cylindrical, elongated structure with a substantially constant outer diameter and rounded, tapered ends for easy positioning by means of a catheter in a blood vessel, e.g., the aorta.

Figure 2:
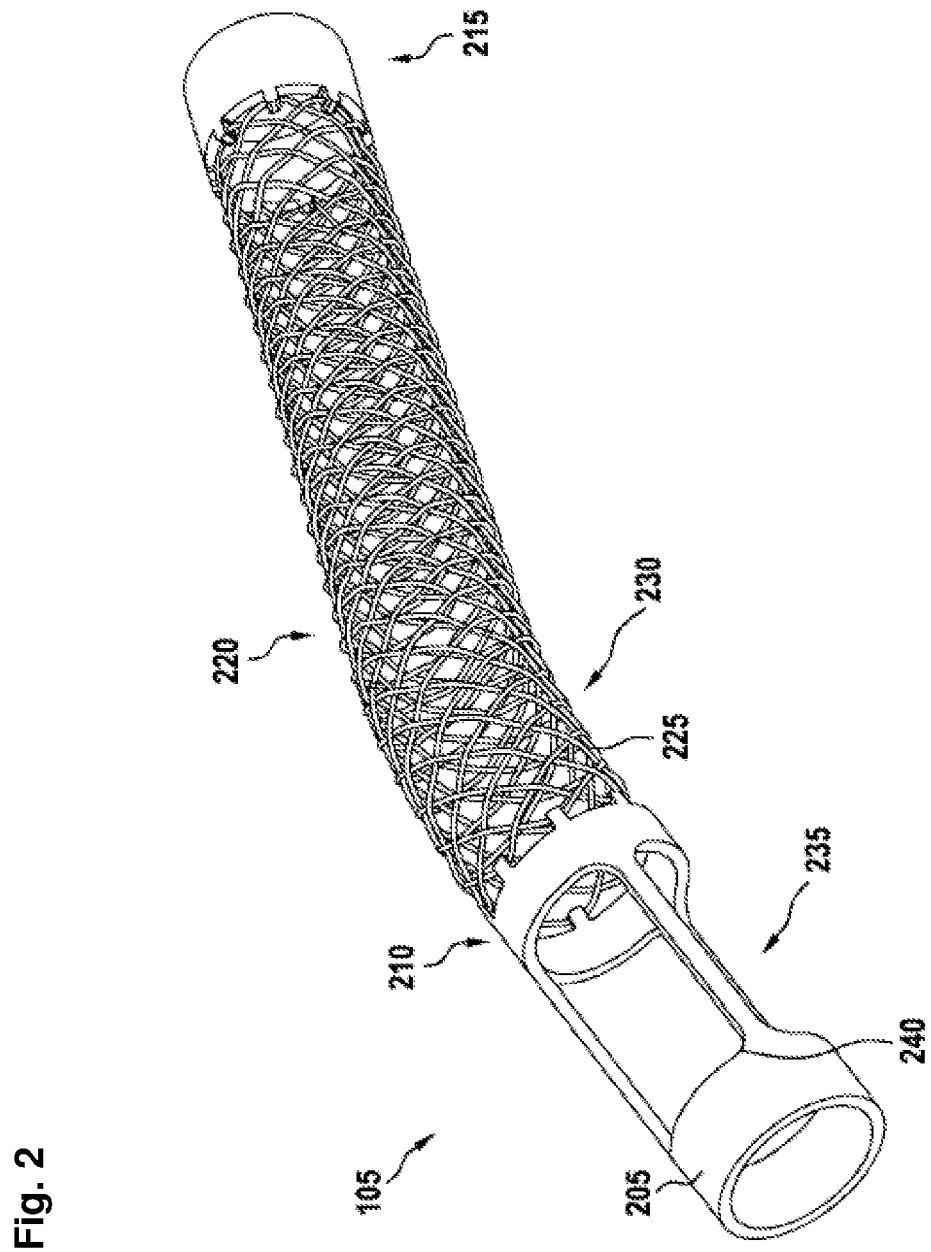
FIG. 2 a schematic illustration of a line device for conducting a blood flow for a heart support system according to an exemplary embodiment.

FIG. 2 shows a schematic illustration of a line device 105 for conducting a blood flow for a heart support system according to an exemplary embodiment in a side view. The line device 105 can also be referred to as a braided suction tube. The line device 105 has a main part 205. The main part 205 is formed in a tubular shape, for example. The main part 205 has, at a first end, a first attachment section 210 for attaching the line device 105 to a head unit of the heart support system and, at a second end, a second attachment section 215 for attaching the line device 105 to an outlet unit of the heart support system. In addition, the main part 105 has a mesh section 220 between the attachment sections 210, 215. The mesh section 220 has a mesh structure 230 formed from at least one mesh wire 225, wherein the main part 205 has an inlet section 235, arranged in the first attachment section 210, for introducing the blood flow into the main part 205. The line device 105 shown here can, for example, be similar or correspond to the line device shown in FIG. 1. The line device 105 is formed to be connectable to adjacent components of the heart support system as shown in FIG. 1. At the first attachment section 210, the line device 105 is formed to be connectable to a head unit of the heart support system and at the second attachment section 215, it is formed to be connectable to an outlet unit of the heart support system.

According to the exemplary embodiment shown here, the inlet section 235 has at least one inlet opening 240 cut in the first attachment section 210. Here, the inlet opening 240 is realized by way of example as a multi-part window. For the inflow of the blood, the inlet section 235 has three rectangularly formed inlet openings 240, which are rounded in the direction of the mesh section 220 in the form of a circular arc.

According to the exemplary embodiment shown here, the mesh structure 230 is formed as a diamond lattice. For this purpose, the at least one mesh wire 225 is braided as a lattice and has a plurality of diamond meshes that form the mesh structure 230.

The line device 105 is shown here with a braided flow channel as mesh section 220. According to one exemplary embodiment, at least the mesh section 220 is formed from a shape memory material. By way of example, the line device shown here is completely formed from Nitinol. By using Nitinol, the line device 105 is suitable not only for short-term use but also for a service life of over 10 years. In medicine, in particular in the field of cardiovascular medicine, Nitinol material is a proven material for heart valve prostheses, stents, and vascular prostheses, for example. Nitinol combines the advantages of biocompatibility and of the shape memory property that allows even complex structures to be realized in a small installation space as in the mesh section 220 shown here.

The mesh section 220 can be braided to the attachment points 210, 215. For this purpose, the attachment points 210, 215 have, for example, as shown here, a fastening element for threading a section of the mesh wire 225. Additionally or alternatively, the mesh section 220 can, for example, also be glued or soldered to the attachment points 210, 215.

According to the exemplary embodiment shown here, the mesh section 220 extends over at least half of the line device 105 in order to adjust the stiffness of the line device. The line device 105 is formed to allow transfemoral surgery (access via the groin). On the one hand, the line device 105 is thus formed flexibly enough to be able to be pushed through the aortic arch and has, on the other hand, a stiffness in order to be able to be pushed through the blood vessels in the axial direction without kinking. The requirements for flexibility and stiffness of the line device 105 in this regard are adjusted by means of the forming of the mesh section 220. The design of the braided structure adapts the ratio of flexibility and stiffness. Variables in this respect are the number of wire paths of the at least one mesh wire 225, a stiffness and a material thickness of the at least one mesh wire 225, as well as the mesh pattern of the mesh structure 230. The higher the number of wire paths of the at least one mesh wire 225 is, the stiffer is the mesh structure 230. The mesh wire 225 comprises, for example, 12 to 24 wire paths. The larger the wire diameter of the mesh wire 225 is, the stiffer is the mesh structure 230. For example, the wire diameter is between 0.1 millimeters and 0.3 millimeters. In addition, material properties of the mesh wire 225 are important: The higher the modulus of elasticity of the mesh wire 225 is, the stiffer is the mesh structure 230. The mesh wire 225 has an elasticity between 74 GPa and 83 GPa, for example. The mesh type of the mesh structure 230 is also important: the closer the meshes are in the mesh, the stiffer is the mesh.

In the exemplary embodiment shown here, the line device 105 is bent in the direction of the first attachment section 210, wherein the bend is by way of example formed as an obtuse angle with respect to a longitudinal axis of the line device 105. The bending can be realized by heat treating the mesh section 220 made of Nitinol. Due to the shape memory properties of the Nitinol, the line device 105 can be formed by a waveform of the mesh section 220 corresponding to human anatomy in order to allow positioning of the inlet opening of the inlet section 235 in the first attachment section 210 in the middle of the heart chamber.

Figure 3:
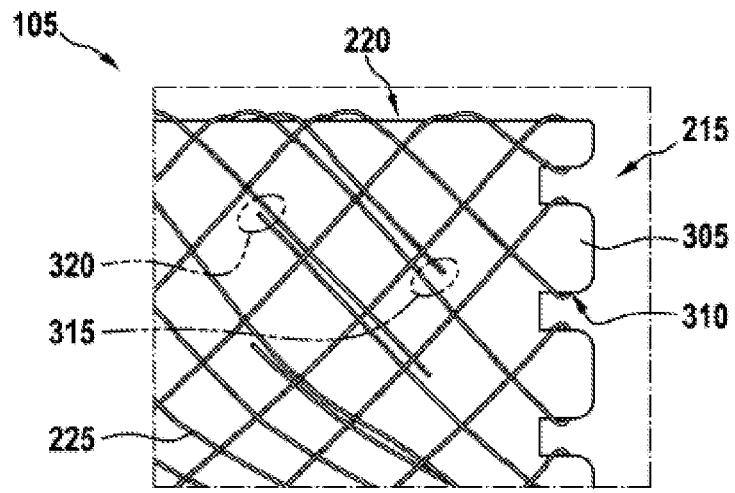
FIG. 3 a schematic illustration of a part of a line device according to an exemplary embodiment.

FIG. 3 shows a schematic illustration of a part of a line device 105 according to an exemplary embodiment. A section of the mesh section 220 connected to the second attachment section 215 is shown in a side view. The first attachment section can be formed like the second attachment section 215 shown here by way of example. The part of the line device 105 shown here is a detail of a similar or corresponding line device as described with reference to FIG. 2.

According to this exemplary embodiment, at least one of the attachment sections, in this case by way of example the second attachment section 215, has at least one eyelet 310 for threading an end of the at least one mesh wire 225 in order to connect the mesh section 220 to the corresponding attachment section. In addition, the first attachment section and/or the second attachment section 215 has at least one merlon 305 as an attachment point for the mesh section 220. The merlon 305 is arranged in particular on the side of the attachment section 215 facing the mesh section 220, as shown here. Optionally, the at least one eyelet 310 is formed in the at least one merlon 305, as shown here.

By way of example, the second attachment section 215 has here a plurality of merlons 305. Each of the merlons 305 has an eyelet 310, through which a section of a mesh wire 225 is guided. In the exemplary embodiment shown here, the structure of the mesh section 220 is formed by way of example from several mesh wires 225. Wire ends of the mesh wires are, for example, integrated into the mesh structure, as indicated by the markings 315 and 320. By means of the mesh wires 225, pump components adjacent through the first and the second attachment section 215, i.e., further components of the heart support system, such as the head unit and the outlet unit, can be connected to the line section 105 permanently and securely. For this purpose, an eyelet 310 into which the mesh wire 225 is threaded is provided for each wire loop of the at least one mesh wire 225. The eyelet 310 can be realized as a bore.

Figure 4:
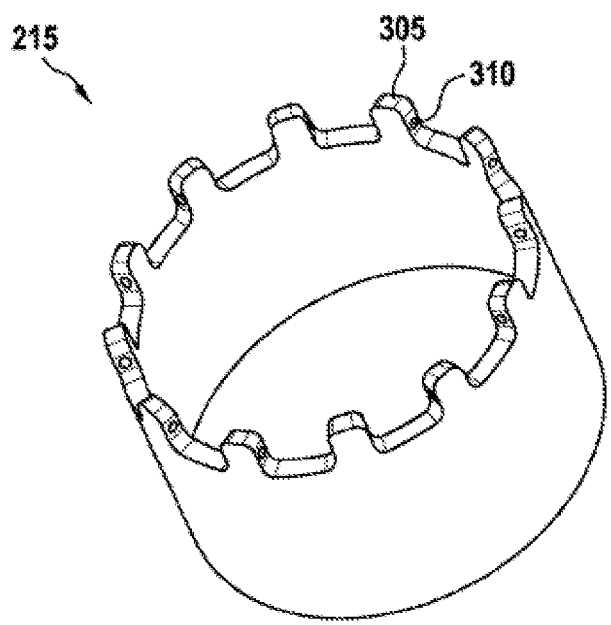
FIG. 4 a schematic illustration of an attachment section of a line device according to an exemplary embodiment.

FIG. 4 shows a schematic illustration of an attachment section of a line device according to an exemplary embodiment. A second attachment section 215 is shown by way of example in a top view. The second attachment section 215 shown here corresponds or is similar to the attachment sections shown in the preceding figures. The at least one mesh wire can be braided into the second attachment section 215. As attachment points for the braiding-in of the mesh wire 225, the second attachment section 215 has a plurality of merlons 305 distributed rotationally evenly on the diameter of the second attachment section 215, i.e., spaced circumferentially evenly. The second attachment section 215 comprises, for example, 6 to 12 merlons 305; 12 merlons 305 are shown here. The eyelets 310 formed in the merlons 305 are realized as bores in the circumferential direction of the cylindrical second attachment section 215 in order to allow tangential threading of the mesh wire 225 in order to not increase the total diameter of the line device 105.

Figure 5:
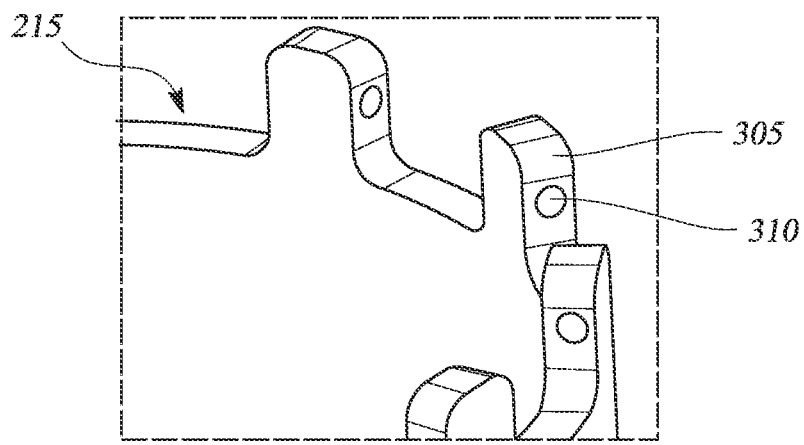
FIG. 5 a schematic illustration of a part of an attachment section of a line device according to an exemplary embodiment.

FIG. 5 shows a schematic illustration of a part of an attachment section 215 of a line device according to an exemplary embodiment. The part shown here is a detail of the second attachment section 215 shown in the preceding FIG. 4. In the detail shown here, each of the merlons 305 has an exposed eyelet 310 as a single attachment point, into which the mesh wire can be tangentially inserted. The eyelets 310 each run transversely with respect to the longitudinal axis of the line device through the merlons 305.

Figure 6:
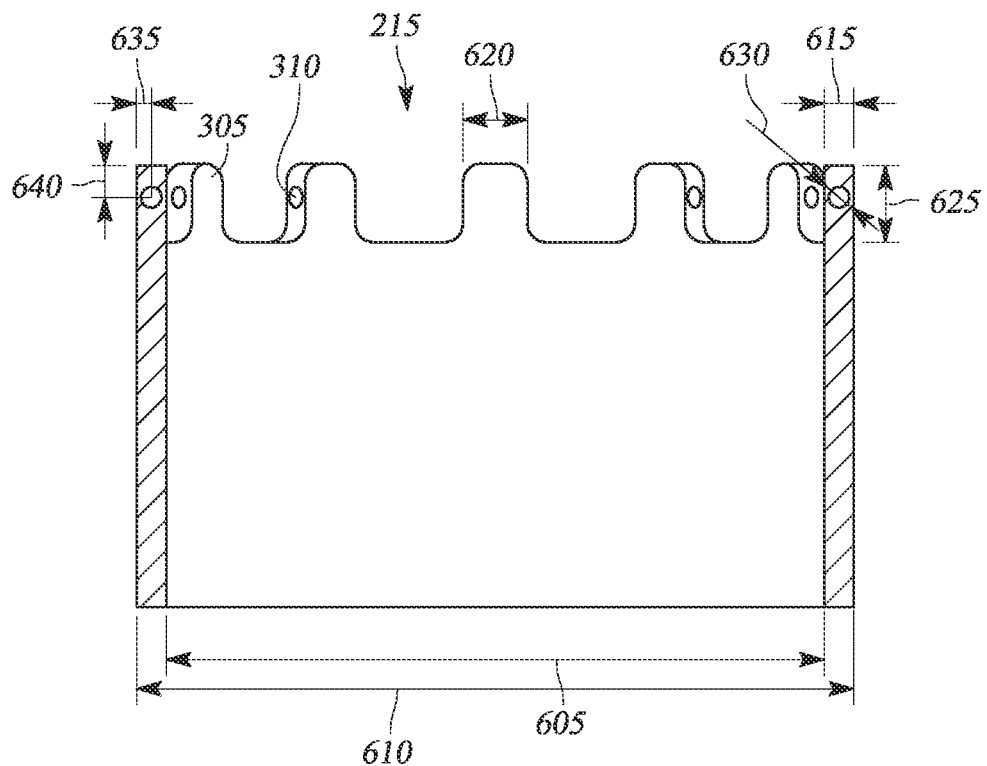
FIG. 6 a schematic illustration of an attachment section of a line device according to an exemplary embodiment.

FIG. 6 shows a schematic illustration of an attachment section 215 of a line device according to an exemplary embodiment. The cross section of a second attachment section 215 is shown in order to illustrate exemplary dimensions of the second attachment section 215. The second attachment section 215 shown corresponds to or is similar to the second attachment section 215 of one of the figures described above. The first attachment section can be formed similarly or correspondingly. The second attachment section 215 has, for example, an inner diameter of 5.5 millimeters indicated by the marking 605 and an outer diameter of 6 millimeters indicated by the marking 610. The merlons 305 have a wall thickness of 0.25 millimeters, which the marking 615 indicates, a width of 0.5 millimeters indicated by the marking 620, and a height of 0.6 millimeters indicated by the marking 625. Each merlon 305 has an eyelet 310 with an inner diameter of 0.15 millimeters, as indicated by the marking 630. The distance from the outer wall of the merlon 305 to the center point of the eyelet 310 is, for example, 0.25 millimeters, as the marking 635 indicates, and the distance from the center point of the eyelet 310 to an upper free end of the merlon 305 is also 0.25 millimeters, as indicated by the marking 340. The bore diameter of each eyelet 310 is somewhat larger than the thickness of the mesh wire in order to allow a wire end to be inserted and the mesh wire to be braided in. The eyelets 310 can be drilled by means of a laser drilling method.

Figure 7:
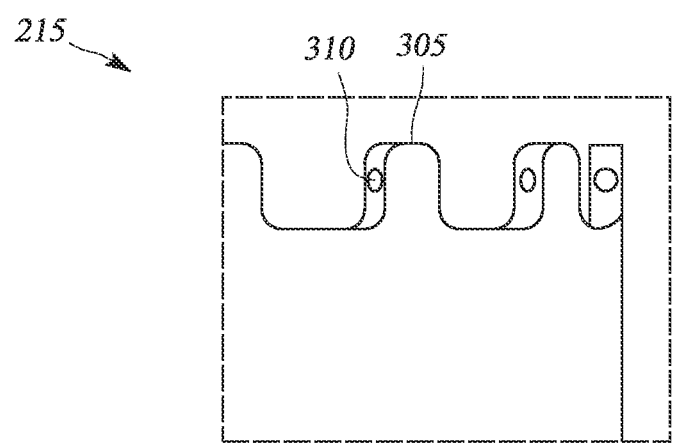
FIG. 7 a schematic illustration of a part of an attachment section of a line device according to an exemplary embodiment.

FIG. 7 shows a schematic illustration of a part of an attachment section of a line device according to an exemplary embodiment. The part shown here is a further detail of the second attachment section 215 shown in FIG. 4, wherein a side view of the detail is shown here. The exemplary shape of the eyelets 310 shown here and the arrangement of the eyelets 310 and merlons 305 allow radial tangential access. The eyelets 310 and the merlons 305 are arranged and dimensioned such that a radial-tangential laser access path is possible when producing the second attachment section 215.

Figure 8:
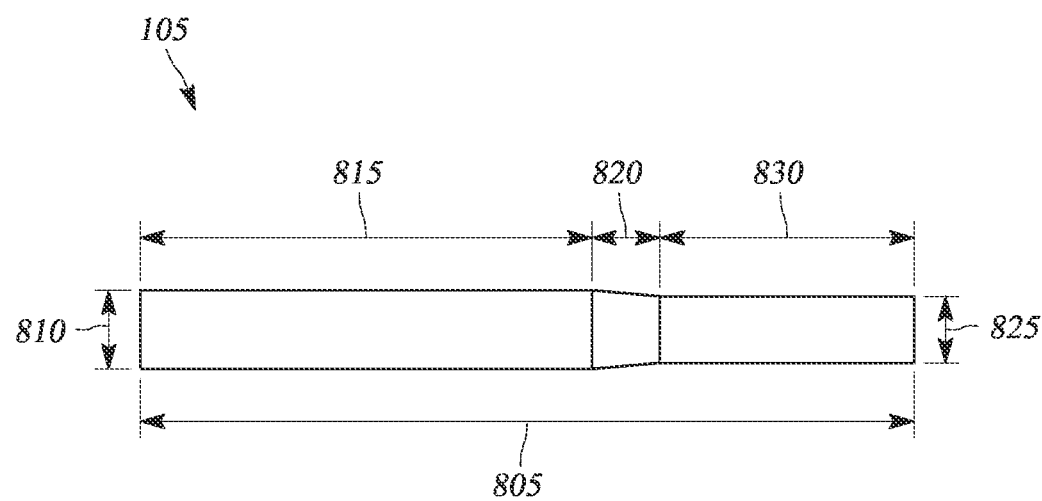
FIG. 8 a schematic illustration of a line device according to an exemplary embodiment.

FIG. 8 shows a schematic illustration of a line device 105 according to an exemplary embodiment. The line device 105 corresponds or is similar to the line device of one of the figures described above. Shown is a change in an inner diameter of the main part of the line device 105, which is illustrated using exemplary dimensions of the line device 105. The main part of the line device 105 has a length of 62 millimeters illustrated by the marking 805. According to the exemplary embodiment shown here, an inner diameter of the main part changes from the first attachment section to the second attachment section. The cross section of the first attachment section has a diameter of 6 millimeters, as indicated by the marking 810. The marking 815 indicates a length of 35 millimeters of a section of the main part with the first attachment section with an inner diameter of 6 millimeters throughout. In the section marked by the marking 820, which has a length of 5 millimeters and adjoins the section of the marking 815, the inner diameter of the line device 105 tapers from 6 millimeters to 5.5 millimeters, as indicated by the marking 825. Over the remaining length, indicated by the marking 830, of 22 millimeters of the main part of the line device 105 shown here, the inner diameter remains constant at 5.49 millimeters. The change in the inner diameter of the main part shown here can improve the flow properties of the blood flow. For this purpose, different diameters in the axial direction can be embossed into the line device 105 as shown here. The inner diameter can in particular be larger in the region with the first attachment section indicated by way of example by the marking 815 than in the region with the second attachment section indicated by the marking 830. In the region corresponding to the marking 815, a larger installation space can, for example, be available than in the region indicated by the marking 830 if the region 830 is, for example, enclosed by a further structural element, for example a sleeve, for inserting the heart support system into a catheter when implanting the heart support system. The braided contour of the mesh section of the line device 105 as a Nitinol element can be formed within the scope of a heat treatment into a predefined shape with, for example, different diameters as shown here. The embossing process in this case describes a plastic deformation without the occurrence of material failure.

Figure 9:
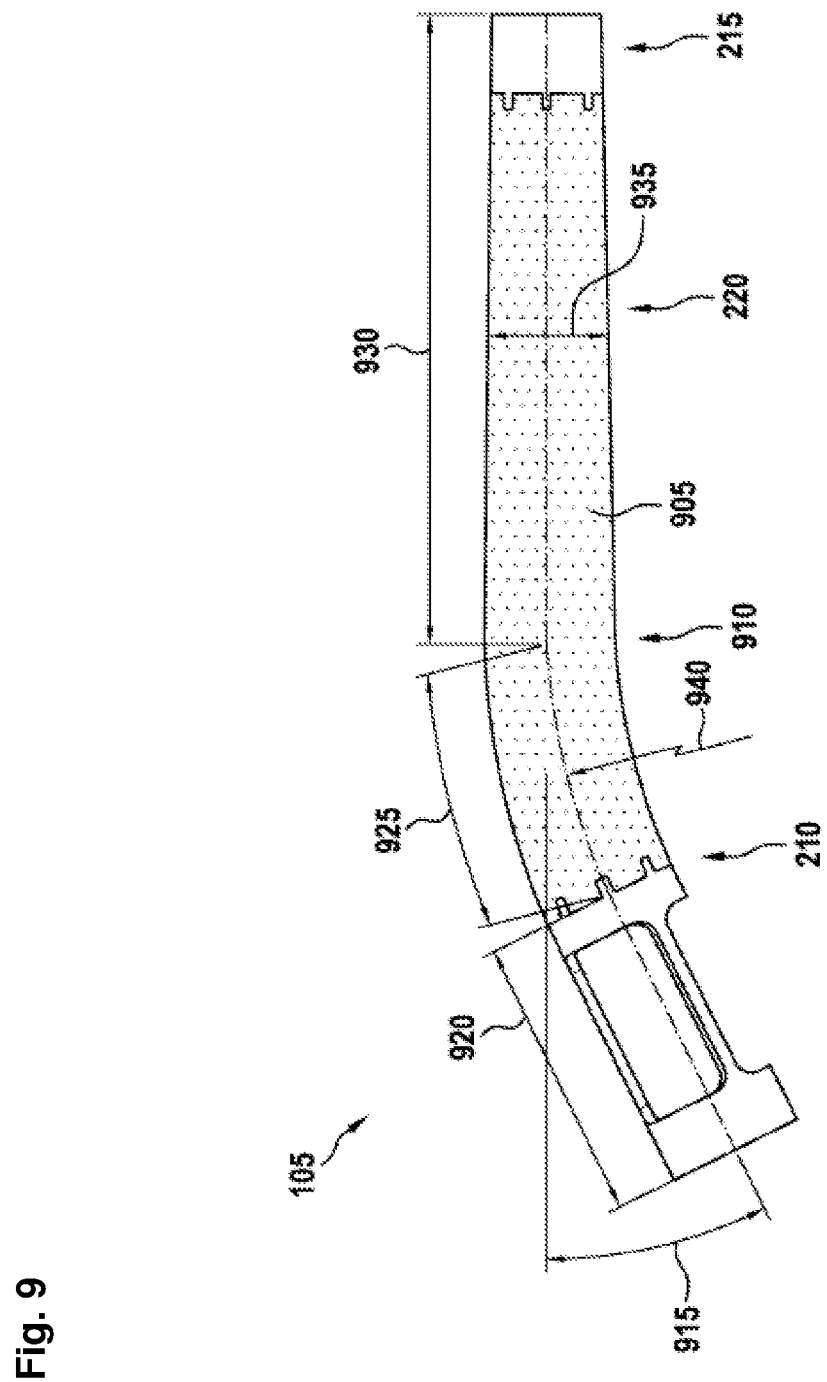
FIG. 9 a schematic illustration of a line device according to an exemplary embodiment.

FIG. 9 shows a schematic illustration of a line device 105 according to an exemplary embodiment. A side view of the line device 105 is shown. By means of markings, this figure illustrates exemplary dimensions of the line device 105 as a suction tube. The line device 105 substantially corresponds to the line device described with reference to FIG. 2, with the exception of a sealing layer 905 arranged on the mesh section 220. According to the exemplary embodiment shown here, the line device 105 comprises the sealing layer 905. The sealing layer 905 is arranged on or in the mesh section 220. The sealing layer 905 is formed to seal the mesh section 220 in a fluid-tight manner. By way of example, the sealing layer 905 is shown here as a silicone casting.

According to the exemplary embodiment shown here, the mesh section 220 furthermore has a bending point 910. The mesh section 220 is in particular bent at an obtuse angle at the bending point, here by way of example by 26 degrees as indicated by the marking 915. The first attachment section 210 has a length of 15.4 millimeters indicated by the marking 920. The section, indicated by the marking 925, of the mesh section 220 with the bending point 910 has a length of 13.6 millimeters, and the remaining section of the main part with a second part of the mesh section 220 and the second attachment section has a length of 33 millimeters as indicated by the marking 930. At the point indicated by the marking 935, the mesh section has a bend of 2 degrees.

Figure 10:
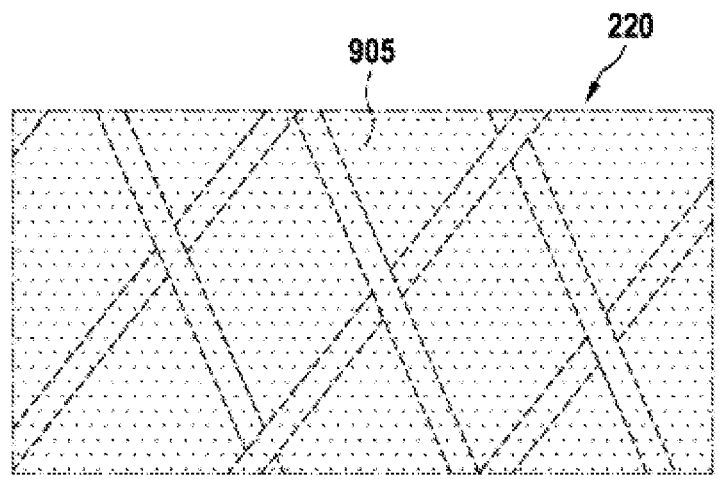
FIG. 10 a schematic illustration of a part of a line device according to an exemplary embodiment.

FIG. 10 shows a schematic illustration of a part of a line device according to an exemplary embodiment. A top view of a detail of the mesh section 220 with a sealing layer 905 is shown. The mesh section 220 is shown as a wire mesh structure, and is, by way of example, cast with a plastic as a sealing layer 905. The sealing layer 905 seals the mesh section 220 in a fluid-tight manner so that the blood flow in the inlet section can be sucked in and pumped through the line device 105, along the mesh section 220, into the outlet unit and thus into the aorta without loss. The sealing layer 905 is formed from a plastic, e.g., polyurethane or silicone, which is still soft enough after curing to withstand the movements of the line device 105 during operation of the heart support system. When the heart support system, in particular the line device 105, is pushed through the aortic arch during surgery, cracks are prevented from forming in the plastic of the sealing layer 905 as a result of a correspondingly selected material of the sealing layer 905.

Figure 11:
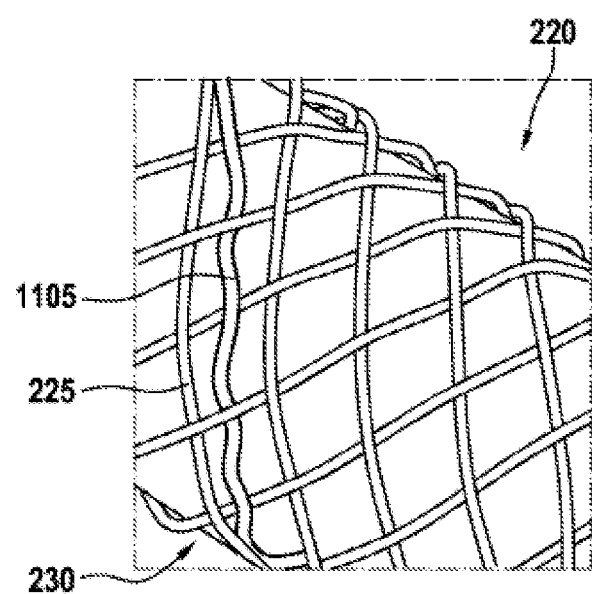
FIG. 11 a schematic illustration of a part of a line device according to an exemplary embodiment.

FIG. 11 shows a schematic illustration of a part of a line device according to an exemplary embodiment. A detail of a section of a mesh section 220 is shown. The mesh section 220 substantially corresponds to the mesh section 220 shown in the preceding figures. In addition, the mesh section 220 according to the exemplary embodiment shown here is formed to receive a cable element 1105 of the heart support system, and, additionally or alternatively, the mesh section 220 is formed to guide a cable element 1105 of the heart support system. As shown here, the mesh structure 230 is optionally formed from the at least one mesh wire 225 and the cable element 1105. The wire mesh of the mesh structure 230 thus comprises an additionally braided-in cable as a cable element 1105. The cable element 1105 can be designed as a section of a cable that allows an electrical data and energy connection from the head unit, e.g., a sensor tip, to the pump of the heart support system. If the head unit 110 of the heart support system has a sensor 1110, for example, the cable element 1105 can be part of a sensor cable. If the mesh structure 230 is formed from several mesh wires 225, a mesh wire 225 is optionally exchanged for the cable element 1105 and the cable element 1105 is braided in in a break-proof manner. If the mesh section 220 has a sealing layer, the sealing layer is an additional mechanical protection of the cable element 1105.

Alternatively, as a replacement of a Nitinol wire as a mesh wire 225, the cable element 1105 is already integrated in the weaving process during the production of the mesh structure 230. Used for this purpose is in particular a round cable, which has similar geometric diameters and mechanical properties as the mesh wire 225 and a thermal resistance for the subsequent heat treatment. Alternatively, the cable is furthermore guided along the outer or inner side of the mesh section without being braided in, as shown in FIG. 12.

Figure 12:
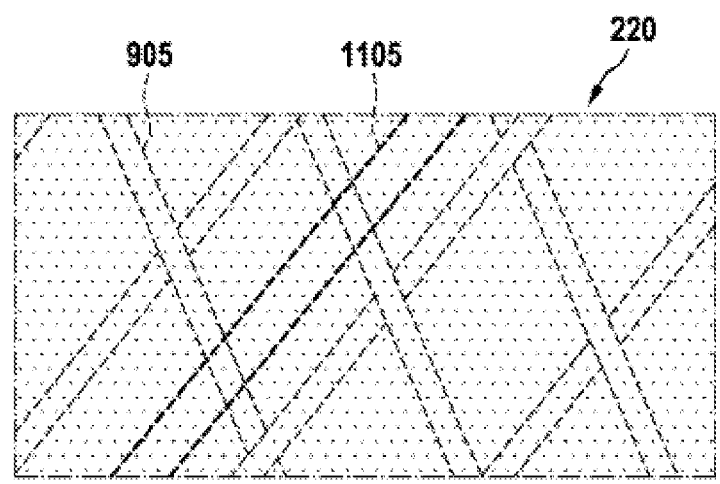
FIG. 12 a schematic illustration of a part of a line device according to an exemplary embodiment.

FIG. 12 shows a schematic illustration of a part of a line device according to an exemplary embodiment. The illustration is similar or corresponds to the illustration of the detail of the line device described with reference to FIG. 10.

In addition, the detail of the mesh section 220 shown here with the sealing layer 905 comprises the cable element 1105. The mesh section 220 is shown by way of example as a wire mesh with an applied and cast flat ribbon cable as a cable element 1105. The cable element 1105 is arranged circumferentially in the shape of a spiral around the longitudinal axis of the mesh section 220, it is glued here and cast or injection-molded with the sealing layer 905, i.e., surrounded by the sealing layer 905. In order to keep the mechanical stresses on the cable element 1105 low, the braided wire slope of the mesh wire is used here by way of example for routing the cable element 1105 in a spiral shape and for fastening the cable element 1105.

Figure 13:
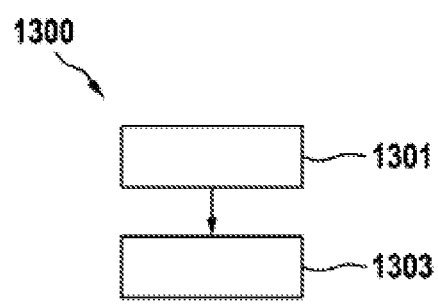
FIG. 13 a flow diagram of a method for producing a line device for conducting a blood flow for a heart support system according to an exemplary embodiment.

FIG. 13 shows a flow diagram of a method 1300 for producing a line device for conducting a blood flow for a heart support system according to an exemplary embodiment. The heart support system has a head unit and an outlet unit. The method 1300 comprises a step 1301 of forming and a step 1303 of heat treating. In step 1301 of forming, a main part is formed from a semi-finished product made of a shape memory material. The main part has, at a first end, a first attachment section for attaching the line device to the head unit and, at a second end, a second attachment section for attaching the line device to the outlet unit. The main part additionally has a mesh section between the attachment sections. The mesh section has a mesh structure formed from at least one mesh wire. Furthermore, the main part has an inlet section, arranged in the first attachment section, for introducing the blood flow into the main part. In step 1303 of heat treating, the main part formed in step 1301 is heat treated in order to emboss a predefined shape into the main part.

If an exemplary embodiment includes an "and/or" conjunction between a first feature and a second feature, this should be read to mean that the exemplary embodiment according to one embodiment comprises both the first feature and the second feature and according to another embodiment comprises either only the first feature or only the second feature.

The invention claimed is:

1. A heart support system comprising:
 a head unit;
 an outlet unit; and
 a line device arranged between the head unit and the outlet unit and configured to conduct a blood flow for the heart support system, wherein the line device comprises:
  a main part comprising:
   a first section at a first end, the first end configured to attach to the head unit;
   a second section at a second end, the second end configured to attach to the outlet unit;
   a mesh section between the first section and the second section, wherein the mesh section comprises a mesh structure formed from at least one mesh wire, wherein the mesh section is configured to receive and/or guide a cable element of the heart support system, and wherein the mesh section is bent at an obtuse angle at a bending point; and
   an inlet arranged in the first section and configured to introduce the blood flow into the main part;
  wherein the head unit comprises a sensor connected to the cable element.

2. The heart support system according to claim 1, wherein at least one of the first section and the second section comprises at least one eyelet configured to thread an end of the at least one mesh wire so as to connect the mesh section to the at least one of the first section and the second section.

3. The heart support system according to claim 1, wherein the mesh structure is formed as a diamond lattice.

4. The heart support system according to claim 1, wherein the mesh structure is formed from the at least one mesh wire and the cable element.

5. The heart support system according to claim 1, wherein at least the mesh section is formed of a shape memory material.

6. The heart support system according to claim 1, wherein the mesh section extends over at least half of the main part to adjust the stiffness of the main part.

7. The heart support system according to claim 1, wherein the line device further comprises a sealing layer arranged on or in the mesh section, wherein the sealing layer is configured to seal the mesh section in a fluid-tight manner.

8. The heart support system according to claim 1, wherein an inner diameter of the main part changes between the first section and the second section.

9. The heart support system according to claim 1, wherein the inlet comprises at least one inlet opening cut in the first section.

10. A heart support system comprising:
 a head unit;
 an outlet unit; and
 a line device arranged between the head unit and the outlet unit and configured to conduct a blood flow for the heart support system, wherein the line device comprises:
  a main part comprising:
   a first section at a first end, the first end configured to attach to the head unit;
   a second section at a second end, the second end configured to attach to the outlet unit;
   a mesh section between the first section and the second section, wherein the mesh section comprises a mesh structure formed from at least one mesh wire, and wherein the mesh section is bent at an obtuse angle at a bending point; and
   an inlet arranged in the first section and configured to introduce the blood flow into the main part;
  wherein the first section and/or the second section comprises at least one merlon, wherein the at least one merlon is arranged on a side of the first section and/or the second section facing the mesh section.

11. The heart support system according to claim 10, wherein at least one of the first section and the second section comprises at least one eyelet configured to thread an end of the at least one mesh wire so as to connect the mesh section to the at least one of the first section and the second section, wherein the at least one eyelet is formed in the at least one merlon.

12. A heart support system comprising:
 a head unit;
 an outlet unit; and
 a line device arranged between the head unit and the outlet unit and configured to conduct a blood flow for the heart support system, wherein the line device comprises:
  a main part comprising:
   a first section at a first end, the first end configured to attach to the head unit;
   a second section at a second end, the second end configured to attach to the outlet unit;
   a mesh section between the first section and the second section, wherein the mesh section comprises a mesh structure formed from at least one mesh wire, wherein the mesh section is configured to receive and/or guide a cable element of the heart support system, and wherein the mesh section extends over at least half of the main part to adjust the stiffness of the main part; and an inlet arranged in the first section and configured to introduce the blood flow into the main part, wherein the head unit comprises a sensor connected to the cable element.

13. The heart support system according to claim 12, wherein at least one of the first section and the second section comprises at least one eyelet configured to thread an end of the at least one mesh wire to connect the mesh section to the at least one of the first section and the second section.

14. The heart support system according to claim 12, wherein the mesh structure is formed as a diamond lattice.

15. The heart support system according to claim 12, wherein the mesh structure is formed from the at least one mesh wire and the cable element.

16. The heart support system according to claim 12, wherein at least the mesh section is formed of a shape memory material.

17. The heart support system according to claim 12, wherein the line device further comprises a sealing layer arranged on or in the mesh section, wherein the sealing layer is configured to seal the mesh section in a fluid-tight manner.

18. The heart support system according to claim 12, wherein an inner diameter of the main part changes between the first section and the second section.

19. The heart support system according to claim 12, wherein the inlet comprises at least one inlet opening cut in the first section.

20. A heart support system comprising:
a head unit;
an outlet unit; and
a line device arranged between the head unit and the outlet unit and configured to conduct a blood flow for the heart support system, wherein the line device comprises:
  a main part comprising:
    a first section at a first end, the first end configured to attach to the head unit;
    a second section at a second end, the second end configured to attach to the outlet unit;
    a mesh section between the first section and the second section, wherein the mesh section comprises a mesh structure formed from at least one mesh wire, and wherein the mesh section extends over at least half of the main part to adjust the stiffness of the main part; and
  an inlet arranged in the first section and configured to introduce the blood flow into the main part,
wherein the first section and/or the second section comprises at least one merlon, wherein the at least one merlon is arranged on a side of the first section and/or the second section facing the mesh section.

21. The heart support system according to claim 20, wherein at least one of the first section and the second section comprises at least one eyelet configured to thread an end of the at least one mesh wire to connect the mesh section to the at least one of the first section and the second section, wherein the at least one eyelet is formed in the at least one merlon.

22. A method for producing a line device for conducting a blood flow for a heart support system, wherein the method comprises:
forming a main part of the line device from a semi-finished product made of a shape memory material, wherein the main part comprises:
  a first section at a first end, the first end configured to attach to a head unit of the heart support system;
  a second section at a second end, the second end configured to attach to an outlet unit of the heart support system;
  a mesh section between the first section and the second section, wherein the mesh section is configured to receive and/or guide a cable element of the heart support system, and wherein the mesh section comprises a mesh structure formed from at least one mesh wire; and
  an inlet arranged in the first section and configured to introduce the blood flow into the main part; and
heat treating the formed main part in order to emboss a predefined shape into the main part, wherein the predefined shape comprises a bend in the mesh section at an obtuse angle at a bending point,
wherein the head unit comprises a sensor connected to the cable element.

* * * * *